(12) United States Patent
Henry et al.

(10) Patent No.: US 7,304,137 B2
(45) Date of Patent: Dec. 4, 2007

(54) NUCLEOTIDE AND AMINO ACID SEQUENCES OF ASPORINS

(75) Inventors: Stephen P. Henry, Houston, TX (US); A. O. Magnus Hook, Houston, TX (US); Richard Mayne, Birmingham, AL (US)

(73) Assignee: The Texas A & M University System, College Station, TX (US)

( * ) Notice: Subject to any disclaimer, the term of this patent is extended or adjusted under 35 U.S.C. 154(b) by 509 days.

(21) Appl. No.: 10/319,130

(22) Filed: Dec. 13, 2002

(65) Prior Publication Data

US 2003/0148351 A1    Aug. 7, 2003

Related U.S. Application Data

(60) Provisional application No. 60/341,537, filed on Dec. 13, 2001.

(51) Int. Cl.
    *C07K 14/435* (2006.01)
(52) U.S. Cl. ..................................... 530/350
(58) Field of Classification Search ................ 530/350
    See application file for complete search history.

(56) References Cited

U.S. PATENT DOCUMENTS 6,380,362 B1 * 4/2002 Watson et al. .............. 530/350

OTHER PUBLICATIONS

Chou, K. C., Prediction of protein signal sequences and their cleavage sites. Proteins 42 (1):136-139, Jan. 1, 2001.*
Henry SP, et al., "Expression Patern and gene characterization of asporin—A newly discovered member of the leucine-rich repeat protein family," *J. Biol. Chem.*; vol. 276 (15); pp. 12212-12221; Apr. 13, 2001.
The RIKEN Genome Exploration Research Group Phase II Team and FANTOM Consortium; "Functional annotation of a full-length mouse cDNA collection;" *Nature* vol. 409, pp. 685-690; Feb. 8, 2001.
Lorenzo, P., et al.; "Identification of Asporin—A novel member of the leucine-rich repeat protein family closely related to decorin and biglycan," *J. Biol. Chem.* vol. 276 (15), pp. 12201-12211; Apr. 13, 2001.
Yamada, S. et al., "Expression profile of active genes in human periodontal ligament and isolation of PLAP-1, a novel SLRP family gene" *Gene* vol. 275 (2), pp. 279-286; Sep. 19, 2001.
Krusious, T. and Ruoslahti, E.; "Primary Structure of an Extracellular matrix proteoglycan core protein deduced from cloned cDNA," *Proc. Natl. Acad. Sci. USA*, vol. 83(20), pp. 7683-7687; Oct. 1986.
Wegrowski, Y., et al.; "The Murine Biglycan : Complete cDNA Cloning, Genomic Organization, Promoter Function, and Expression," *Genomics* vol. 30(1), pp. 8-17; Nov. 1, 1995.
Scholzen, T., et al., "The Murine Decorin—Complete cDNA Cloning, Genomic Organization, Chromosomal Assignment, and Expression During Organogenesis and Tissue Differentiation" *J. Biol. Chem.*, vol. 269(45), pp. 28270-28281; Nov. 11, 1994.
GenBank AI006670; Jun. 12, 1998.
GenBank AI539334; Apr. 13, 1998.
GenBank AK000136; Feb. 22, 2000.
GenBank BC034888; Sep. 20, 2002.
GenBank NW_000075; Nov. 17, 2002.
GenBank AK000236; Feb. 22, 2000.
GenBank NM_025711; Jan. 7, 2002.

* cited by examiner

*Primary Examiner*—Ruixiang Li
(74) *Attorney, Agent, or Firm*—Benjamin Aaron Adler

(57) ABSTRACT

Mouse asporin protein and nucleic acid sequences are disclosed. The protein contains a unique aspartic acid region near the N-terminus. The central domain contains ten leucine rich repeats. Sequences consistent with other class I small leucine rich repeat proteoglycans (SLRP) are also observed. Methods of use for the protein include regulating the complement system, inhibiting fibrosis formation, regulating the growth of endothelial cells and angiogenesis, regulating or inhibiting the growth of cancer cells, and regulating the functions of neuromuscular junctions.

1 Claim, 11 Drawing Sheets

```
                     ACAAACAGTGATGGAAAACATATGAGCAGTAACAAGTTTTAATCTCGCTCTTCAGTACTAAC    62
ATGGACTAATCTGTGGAAGCAGTTTATTCCAGTATCACCCAGGAGCAGCCACACAGAGGCTGGTAGGAGGGCTGGATTTTT   143
GTTCTCTTTTTTTCTTTTCTTTAAATGTAACACTTCTTTATTTTTTCTTCTTGAAGAGTCTTGAGGATACTTACATTGCAG   224
TTAAGTAGTACAGGGTGGATAAATTCTACTTTGAAGAAAACTTCTCTCCTCTGACAAGGTTGGACTTGTACACAGGCCAGC   305

ATGAAGGAGTATGTGATGCTACTGCTTTTGGCTGTGTGCTCTGCCAAACCCTTCTTTAGCCCTTCCCACACAGCACTGAAG   386
 M  K  E  Y  V  M  L  L  L  A  V  C  S  A  K  P  F  F  S  P  S  H  T  A  L  K       27
                                          ↑
AATATGATGTTGAAGGATATGGAAGACACAGATGATGACGATAACGATGATGACGACAACTCTCTTTTTCCAACGAAAGAG   467
 N  M  M  L  K  D  M  E  D  T  D  D  D  D  N  D  D  D  D  N  S  L  F  P  T  K  E    54
                 ●●●●●●●●●●●●●●●●●●● ACIDIC STRETCH ●●●●●●●●●●●●●●●
CCAGTGAACCCTTTTTTCCCTTTCGATTTGTTTCCAACATGTCCATTTGGGTGCCAATGTTACTCTCGAGTTGTTCACTGC   548
 P  V  N  P  F  F  P  F  D  L  F  P  T [C] P  F  G [C] Q [C] Y  S  R  V  V  H [C]   81

TCTGATCTAGGTCTGACATCGGTTCCAAACAACATTCCATTTGATACTCGAATGGTTGACCTTCAAAATAATAAAATCAAG   629
 S  D  L  G  L  T  S  V  P  N  N  I  P  F  D  T  R  M  V  D  L  Q  N  N  K  I  K   108
                                               LRR1
GAAATTAAAGAAAATGACTTTAAAGGACTCACTTCACTTTATGCTCTGATTCTGAACAACAACAAGCTAACAAAGATTCAC   710
 E  I  K  E  N  D  F  K  G  L  T  S  L  Y  A  L  I  L  N  N  N  K  L  T  K  I  H   135
                                   LRR2
CCAAAAACCTTTCTAACCACAAAGAAATTGAGAAGGCTATATTTATCCCACAACCAACTAAGTGAAATTCCACTTAATCTT   791
 P  K  T  F  L  T  T  K  K  L  R  R  L  Y  L  S  H  N  Q  L  S  E  I  P  L  N  L   162
                              LRR3
CCCAAATCATTAGCAGAACTCAGAATTCATGATAATAAAGTTAAGAAGATACAAAAGGACACGTTCAAGGGAATGAATGCT   872
 P  K  S  L  A  E  L  R  I  H  D  N  K  V  K  K  I  Q  K  D  T  F  K  G  M  N  A   189
           LRR4
TTACATGTTTTGGAAATGAGTGCAAACCCTCTTGAGAACAACGGGATAGAACCAGGGGCATTTGAAGGGGTGACAGTATTC   953
 L  H  V  L  E  M  S  A  N  P  L  E  N  N  G  I  E  P  G  A  F  E  G  V  T  V  F   216
      LRR5
CATATCAGGATCGCTGAAGCAAAACTAACCTCAATTCCAAAAGGCCTACCACCAACTTTGCTGGAGCTTCATTTAGATTTT  1034
 H  I  R  I  A  E  A  K  L  T  S  I  P  K  G  L  P  P  T  L  L  E  L  H  L  D  F   243
       LRR6                                          LRR7
AATAAAATTTCAACGGTGGAACTTGAAGATCTTAAACGGTACAGGGAACTGCAAAGGCTGGGTCTTGGAAACAACAGAATC  1115
 N  K  I  S  T  V  E  L  E  D  L  K  R  Y  R  E  L  Q  R  L  G  L  G  N  N  R  I   270
                                                          LRR8
ACAGATATTGAAAATGGAACTTTTGCTAATATACCACGTGTGAGAGAGATACACTTGGAACACAATAAACTAAAAAAAATC  1196
 T  D  I  E (N) G  T  F  A  N  I  P  R  V  R  E  I  H  L  E  H  N  K  L  K  K  I   297
                                    LRR9
CCTTCAGGATTACAGGAGTTGAAATACCTCCAGATAATCTTCCTTCATTATAATTCAATTGCAAAGTGGGAGTGAATGAC  1277
 P  S  G  L  Q  E  L  K  Y  L  Q  I  I  F  L  H  Y  N  S  I  A  K  V  G  V  N  D   324
                         LRR10
TTCTGTCCAACAGTGCCAAAGATGAAGAAATCTTTATACAGTGCAATAAGTTTATTCAACAACCCAATGAAGTACTGGGAA  1358
 F [C] P  T  V  P  K  M  K  K  S  L  Y  S  A  I  S  L  F  N  N  P  M  K  Y  W  E   351

ATACAACCTGCAACATTTCGTTGTGTTCTTGGCAGAATGAGTGTTCAGCTTGGGAATGTTGGAAAATAA              1427
 I  Q  P  A  T  F  R [C] V  L  G  R  M  S  V  Q  L  G  N  V  G  K  *               373

TTCATGACATCCGTTAAATATAAAATTCAAAAATGTATACATTTGGAATACTTGAACTGTCCTAGTAATGGTAGTATTATA  1508
CACATAAGCAAAATTCTATTCTATATGGTCAATGACAAAAAACTTCAACAGAATTTTGCCTAATTATTGATGCTCAGAATA  1589
AATTTCTATTGCAGTGTCCTTCTGCACATGAATGATTCTTGCGTAAATTTTTGCTTGAACATTCTTTTTTCGGCAAAAAA  1670
AGATATTTAGTATTTAACCCTTCATTATCAAGTCAGTCAAACAGAATTGTACTGTAAACAGAATGCTTGACTTAGTAACAT  1751
TTGTGTCATATCTTTGCTGTTAGAAAAACAAAACTGGCAAGAACAGCATTTTGAAGAGTACATATATTTTTAGTAGTTTTT  1832
TAAAAAAAAACTTGGACAGTACTGTAATGTTTCCAGTAATGTTGGAATACATATAGTTTGACAGAATCAAAATTCTCAACT  1913
CATAATAAAGCTTCAAGTATTCACAGATAATATTCATCAGAGTTGGTTTGGGCTATAACACATGAATATCTTTTTTAAATT  1994
ATTAACTGGCTATAAAATTGTAAAAATAATAATGCTGCTAATAAAATCTATAATGTGCATTTTTATGATCAGTTATATAA  2075
GCTTTGAAGAACCCAGTAACTGTTAGGTTACATAGTGTTATTACTTCAACTAGGAATATTTCAGGATATCCCTTTGGAACA  2156
GTATGGACGCCAATCAATTTTATATCAACTTATCTCTTCAAATATGCACATTGGGTAATGCCTGGAAACATAGCTAAGGTG  2237
ACAAAAACTGAAAACTGAACAAAACTTAATAGTACTTTCATGTGTTTTTTTAAACTGATATTCATTATGAATTAAGTAAA  2318
AAGTGACAATAAGGAAAACATTAAATACTGGTTTTCAAT                                        2357
```

FIGURE 1

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| human asp | 1 | M | K | E | Y | V | L | L | L | F | L | L | A | L | C | S | A | K | P | F | F | S | P | S | H | I | A | L | K | 27 |
| mouse asp | 1 | M | K | E | Y | V | L | L | L | F | L | L | A | L | C | S | A | K | P | F | F | S | P | S | H | T | A | L | K | 27 |
| mouse bgn | 1 | M | C | P | L | W | L | L | T | F | L | L | V | A | L | S | Q | K | P | F | E | K | G | F | W | D | F | T | T | 28 |
| mouse dec | 1 | M | K | A | T | L | F | F | L | L | L | A | Q | A | W | Q | Q | R | G | L | F | Q | F | L | F | D | F | M | M | 28 |

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| human asp | 29 | N | M | F | L | M | E | Y | V | M | L | L | F | L | A | D | D | D | D | D | D | D | D | D | E | D | N | N | S | 55 |
| mouse asp | 29 | N | M | L | L | M | D | M | L | L | L | L | D | D | E | D | D | D | D | D | D | D | D | N | N | – | – | – | – | 48 |
| mouse bgn | 29 | L | D | D | G | D | L | M | M | L | T | D | A | E | D | T | T | S | – | – | – | – | – | – | – | – | – | – | – | 48 |
| mouse dec | 29 | L | E | D | E | A | S | G | I | F | P | Y | D | P | D | T | – | – | – | – | – | – | – | – | – | – | – | – | – | 44 |

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| human asp | 56 | L | F | P | T | R | E | P | T | H | F | F | P | P | R | S | L | F | F | H | M | P | P | G | F | P | Y | S | W | 83 |
| mouse asp | 49 | L | F | P | T | R | E | P | T | F | F | R | S | V | N | L | F | P | T | A | M | C | C | G | Y | T | H | L | L | 76 |
| mouse bgn | 49 | – | K | G | L | K | G | P | V | D | P | D | T | A | L | F | S | H | S | A | C | P | C | H | C | C | P | – | – | 72 |
| mouse dec | 45 | – | – | – | – | – | – | – | – | – | – | – | – | – | – | – | – | – | – | – | – | – | – | – | – | – | – | – | – | 57 |

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| human asp | 84 | R | V | H | C | S | D | L | G | L | D | P | A | V | P | T | N | N | H | P | F | D | T | T | R | M | L | D | Q | 111 |
| mouse asp | 77 | R | V | H | D | L | G | L | L | G | P | N | P | P | P | F | S | N | N | H | P | F | D | T | R | M | V | L | Q | 104 |
| mouse bgn | 73 | R | V | Q | C | S | D | L | G | L | K | D | V | P | T | K | E | D | F | P | S | P | P | T | T | L | L | L | Q | 100 |
| mouse dec | 58 | R | V | Q | C | S | D | L | G | L | W | D | K | V | P | D | W | F | P | P | F | G | A | T | T | L | H | H | Q | 85 |

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| human asp | 112 | N | K | I | E | E | H | M | L | L | G | N | D | F | K | W | S | L | Y | G | L | I | H | L | N | N | K | L | T | 139 |
| mouse asp | 105 | N | K | K | E | I | E | L | L | L | N | D | F | K | E | S | L | Y | A | L | H | H | L | N | K | L | H | S | 132 |
| mouse bgn | 101 | N | D | L | R | D | L | V | L | L | R | D | F | K | E | L | Y | A | L | V | H | L | L | D | K | N | L | S | 128 |
| mouse dec | 86 | N | K | I | T | E | I | K | E | G | A | F | K | N | L | H | T | L | H | T | I | H | L | V | K | N | K | I | S | 113 |

Fig. 2A

```
human asp  140 K I H H P K A F L T T K K L L R L Y L S H N Q L S E I P L 167
mouse asp  133 K I H H P K T F L T P L K K L Y L S H N Q L S E I P L 160
mouse bgn  129 K I H E P K A F S P L K L L Y L S K N Q L V E I P P 156
mouse dec  114 K I S P E A F K P L Q E L R V K L Y L S K N H L K E L P E 141 human asp  168 N L L H P K S L A E L T P L R K L H L E N N K L K S I P K G M N 195
mouse asp  161 N L L H P K S L A E L T P L R K L H L E N N K L K K G M N 188
mouse bgn  157 N L P S S L V E L R L A H N K L Q E D T F K G L R 184
mouse dec  142 K M P R T L Q E L . L E H N Q L K S D F N G L N 169 human asp  196 A L H V L L E M S A N P L D E N N S G V T V F 223
mouse asp  189 A L H V L L E M S A N P L D E N N S G V T V F 216
mouse bgn  185 N M N C I E M G G N P L E N S G F L K N 212
mouse dec  170 N V L V E L L G G N P L K N G I E L S L 197 human asp  224 . H I R I A E A K K L T S V P H H H L H L D Y 250
mouse asp  217 . H I H E A K K L T S V P H H H L D D F 243
mouse bgn  213 . Y L R R T S E A K L T G H H L D H 239
mouse dec  198 S Y H S D T N T A H H L D G 225 human asp  251 N K I S T V E L E D F K K A Y K E L Q R L H I T 278
mouse asp  244 N K I S T V E L E D F K R Y R E K I H T 271
mouse bgn  240 N K I Q A H E D L L R Y S K L Q I R 267
mouse dec  226 N K I T K V D A P S L K G L N S K T 253
```

Fig. 2B

```
human asp 279 D I E N G S L A N I P R V R E I H L E E N N K L K K I P S 306
mouse asp 272 D I E N G T F A N I P R V L R E I H L E H D N K K K I P S 299
mouse bgn 268 M I E N G S L F L P T H L R V L R E L H L L D N K L S R V P A 295
mouse dec 254 V M E N G S L A N V P H L R E L H L L D N N K L R V P P A 281 human asp 307 G L P E L K Y L Q I H I F L H S N S I H I H L E E N D F C P 334
mouse asp 300 G L Q E L K Y L Q I H I F L H Y N S I H I H L E E N D F C P 327
mouse bgn 296 G L P D L K L I Q L H I V V Y L H N N N I T K V N D F C P 323
mouse dec 282 G L A Q H K Y I Q V V V L H N S A V G Q N D F C R 309 human asp 335 T V P K M K K S L Y S A I S L F N N H N P V K Y W E M Q P A 362
mouse asp 328 T V P K M K K S L Y S A I S L F N N M P M K Y W E I Q P A 355
mouse bgn 324 M G F V K R A Y Y N G I S L F N N N P V P Y W E V Q P A 351
mouse dec 310 A G H P S R K A S Y S A V S L Y G N P V R Y W E I F P N 337 human asp 363 T F R C V L S R M S V Q L G N F G M 380  (SEQ ID NO: 18)
mouse asp 356 T F R C V L G R M S V Q L G N V G K 373  (SEQ ID NO: 6)
mouse bgn 352 T F R C V T D R L A I Q F G N Y K K 369  (SEQ ID NO: 19)
mouse dec 338 T F R C V Y V R S A H Q L G N Y K 354  (SEQ ID NO: 20)
```

Fig. 2C

SEQUENCE LISTING

<160> NUMBER OF SEQ ID NOS: 51

<210> SEQ ID NO 1
<211> LENGTH: 2357
<212> TYPE: DNA
<213> ORGANISM: Mus musculus

<400> SEQUENCE: 1

```
acaaacagtg atggaaaaca tatgagcagt aacaagtttt aatctcgctc ttcagtacta     60
acatggacta atctgtggaa gcagtttatt ccagtatcac ccaggagcag ccacacagag    120
gctggtagga gggctggatt tttgttctct ttttttcttt tctttaaatg taacacttct    180
ttattttttc ttcttgaaga gtcttgagga tacttacatt gcagttaagt agtacagggt    240
ggataaattc tactttgaag aaaacttctc tcctctgaca aggttggact tgtacacagg    300
ccagcatgaa ggagtatgtg atgctactgc ttttggctgt gtgctctgcc aaacccttct    360
ttagcccttc ccacacagca ctgaagaata tgatgttgaa ggatatggaa gacacagatg    420
atgacgataa cgatgatgac gacaactctc tttttccaac gaaagagcca gtgaaccctt    480
ttttcccttt cgatttgttt ccaacatgtc catttgggtg ccaatgttac tctcgagttg    540
ttcactgctc tgatctaggt ctgacatcgg ttccaaacaa cattccattt gatactcgaa    600
tggttgacct tcaaaataat aaaatcaagg aaattaaaga aaatgacttt aaaggactca    660
cttcacttta tgctctgatt ctgaacaaca acaagctaac aaagattcac ccaaaaacct    720
ttctaaccac aaagaaattg agaaggctat atttatccca caaccaacta agtgaaattc    780
cacttaatct tcccaaatca ttagcagaac tcagaattca tgataataaa gttaagaaga    840
tacaaaagga cacgttcaag ggaatgaatg ctttacatgt tttggaaatg agtgcaaacc    900
ctcttgagaa caacgggata gaaccagggg catttgaagg ggtgacagta ttccatatca    960
ggatcgctga agcaaaacta acctcaattc caaaaggcct accaccaact ttgctggagc   1020
ttcatttaga ttttaataaa atttcaacgg tggaacttga agatcttaaa cggtacaggg   1080
aactgcaaag gctgggtctt ggaaacaaca gaatcacaga tattgaaaat ggaacttttg   1140
ctaatatacc acgtgtgaga gagatacact tggaacacaa taaactaaaa aaaatccctt   1200
caggattaca ggagttgaaa tacctccaga taatcttcct tcattataat tcaattgcaa   1260
aagtgggagt gaatgacttc tgtccaacag tgccaaagat gaagaaatct ttatacagtg   1320
```

-continued

```
caataagttt attcaacaac ccaatgaagt actgggaaat acaacctgca acatttcgtt    1380
gtgttcttgg cagaatgagt gttcagcttg ggaatgttgg aaaataattc atgacatccg    1440
ttaaatataa aattcaaaaa tgtatacatt tggaatactt gaactgtcct agtaatggta    1500
gtattataca cataagcaaa attctattct atatggtcaa tgacaaaaaa cttcaacaga    1560
attttgccta attattgatg ctcagaataa atttctattg cagtgtcctt ctgcacatga    1620
atgattcttg cgtaaatttt ttgcttgaac attcttttt cggcaaaaaa agatatttag     1680
tatttaaccc ttcattatca agtcagtcaa acagaattgt actgtaaaca gaatgcttga    1740
cttagtaaca tttgtgtcat atctttgctg ttagaaaaac aaaactggca agaacagcat    1800
tttgaagagt acatatattt ttagtagttt tttaaaaaaa aacttggaca gtactgtaat    1860
gtttccagta atgttggaat acatatagtt tgacagaatc aaaattctca actcataata    1920
aagcttcaag tattcacaga taatattcat cagagttggt ttgggctata acacatgaat    1980
atctttttta aattattaac tggctataaa attgtaaaaa tataatgact gctaatataa    2040
aatctataat gtgcatttta tgatcagtta tataagcttt gaagaaccca gtaactgtta    2100
ggttacatag tgttattact tcaactagga atatttcagg atatcccttt ggaacagtat    2160
ggacgccaat caatttttata tcaacttatc tcttcaaata tgcacattgg gtaatgcctg    2220
gaaacatagc taaggtgaca aaaactgaaa actgaacaaa acttaatagt actttcatgt    2280
gtttttttta aactgatatt cattatgaat taagtaaaaa gtgacaataa ggaaaacatt    2340
aaatactggt tttcaat                                                    2357

<210> SEQ ID NO 2
<211> LENGTH: 1119
<212> TYPE: DNA
<213> ORGANISM: Mus musculus

<400> SEQUENCE: 2
atgaaggagt atgtgatgct actgcttttg gctgtgtgct ctgccaaacc cttctttagc      60
ccttcccaca cagcactgaa gaatatgatg ttgaaggata tggaagacac agatgatgac     120
gataacgatg atgacgacaa ctctcttttt ccaacgaaag agccagtgaa ccctttttc      180 cctttcgatt tgtttccaac atgtccattt gggtgccaat gttactctcg agttgttcac     240
tgctctgatc taggtctgac atcggttcca acaacattc catttgatac tcgaatggtt      300
gaccttcaaa ataataaaat caaggaaatt aaagaaaatg actttaaagg actcacttca     360
ctttatgctc tgattctgaa caacaacaag ctaacaaaga ttcacccaaa aacctttcta    420
accacaaaga aattgagaag gctatatttta tcccacaacc aactaagtga aattccactt    480
aatcttccca atcattagc agaactcaga attcatgata taaagttaa gaagatacaa    540 aaggacacgt tcaagggaat gaatgcttta catgttttgg aaatgagtgc aaaccctctt    600
gagaacaacg ggatagaacc aggggcattt gaaggggtga cagtattcca tatcaggatc    660
gctgaagcaa aactaacctc aattccaaaa ggcctaccac caactttgct ggagcttcat    720 ttagattta ataaaatttc aacggtggaa cttgaagatc ttaaacggta cagggaactg    780
caaaggctgg gtcttggaaa caacagaatc acagatattg aaaatggaac ttttgctaat    840
ataccacgtg tgagagagat acacttggaa cacaataaac taaaaaaaat cccttcagga    900
ttacaggagt tgaaataccttccagataatc ttccttcatt ataattcaat tgcaaaagtg    960
ggagtgaatg acttctgtcc aacagtgcca agatgaaga aatctttata cagtgcaata   1020
```

```
agtttattca acaacccaat gaagtactgg gaaatacaac ctgcaacatt tcgttgtgtt    1080
cttggcagaa tgagtgttca gcttgggaat gttggaaaa                          1119

<210> SEQ ID NO 3
<211> LENGTH: 305
<212> TYPE: DNA
<213> ORGANISM: Mus musculus

<400> SEQUENCE: 3
acaaacagtg atggaaaaca tatgagcagt aacaagtttt aatctcgctc ttcagtacta     60
acatggacta atctgtggaa gcagtttatt ccagtatcac ccaggagcag ccacacagag    120
gctggtagga gggctggatt tttgttctct ttttttcttt tctttaaatg taacacttct    180
ttattttttc ttcttgaaga gtcttgagga tacttacatt gcagttaagt agtacagggt    240
ggataaattc tactttgaag aaaacttctc tcctctgaca aggttggact tgtacacagg    300
ccagc                                                               305

<210> SEQ ID NO 4
<211> LENGTH: 930
<212> TYPE: DNA
<213> ORGANISM: Mus musculus

<400> SEQUENCE: 4
ttcatgacat ccgttaaata taaaattcaa aaatgtatac atttggaata cttgaactgt     60
cctagtaatg gtagtattat acacataagc aaaattctat tctatatggt caatgacaaa    120
aaacttcaac agaattttgc ctaattattg atgctcagaa taaatttcta ttgcagtgtc    180
cttctgcaca tgaatgattc ttgcgtaaat ttttgcttg aacattcttt tttcggcaaa     240
aaaagatatt tagtatttaa cccttcatta tcaagtcagt caaacagaat tgtactgtaa    300
acagaatgct tgacttagta acatttgtgt catatctttg ctgttagaaa acaaaaactg    360
gcaagaacag cattttgaag agtacatata tttttagtag ttttttaaaa aaaaacttgg    420
acagtactgt aatgtttcca gtaatgttgg aatacatata gtttgacaga tcaaaattc    480 tcaactcata ataaagcttc aagtattcac agataatatt catcagagtt ggtttgggct    540
ataacacatg aatatctttt ttaaattatt aactggctat aaaattgtaa aaatataatg    600
actgctaata taaaatctat aatgtgcatt ttatgatcag ttatataagc tttgaagaac    660
ccagtaactg ttaggttaca tagtgttatt acttcaacta ggaatatttc aggatatccc    720 tttgaacag tatggacgcc aatcaatttt atatcaactt atctcttcaa atatgcacat     780
tgggtaatgc ctggaaacat agctaaggtg acaaaaactg aaaactgaac aaaacttaat    840
agtactttca tgtgtttttt ttaaactgat attcattatg aattaagtaa aaagtgacaa    900
taaggaaaac attaaatact ggttttcaat                                    930

<210> SEQ ID NO 5
<211> LENGTH: 5
<212> TYPE: DNA
<213> ORGANISM: Mus musculus

<400> SEQUENCE: 5 aataa                                                                 5

<210> SEQ ID NO 6
<211> LENGTH: 373
<212> TYPE: PRT
<213> ORGANISM: Mus musculus
```

<400> SEQUENCE: 6

```
Met Lys Glu Tyr Val Met Leu Leu Leu Ala Val Cys Ser Ala Lys
1               5                   10                  15

Pro Phe Phe Ser Pro Ser His Thr Ala Leu Lys Asn Met Met Leu Lys
            20                  25                  30

Asp Met Glu Asp Thr Asp Asp Asp Asn Asp Asp Asp Asn Ser
        35                  40                  45

Leu Phe Pro Thr Lys Glu Pro Val Asn Pro Phe Phe Pro Phe Asp Leu
    50                  55                  60

Phe Pro Thr Cys Pro Phe Gly Cys Gln Cys Tyr Ser Arg Val Val His
65                  70                  75                  80

Cys Ser Asp Leu Gly Leu Thr Ser Val Pro Asn Asn Ile Pro Phe Asp
                85                  90                  95

Thr Arg Met Val Asp Leu Gln Asn Asn Lys Ile Lys Glu Ile Lys Glu
            100                 105                 110

Asn Asp Phe Lys Gly Leu Thr Ser Leu Tyr Ala Leu Ile Leu Asn Asn
        115                 120                 125

Asn Lys Leu Thr Lys Ile His Pro Lys Thr Phe Leu Thr Thr Lys Lys
    130                 135                 140

Leu Arg Arg Leu Tyr Leu Ser His Asn Gln Leu Ser Glu Ile Pro Leu
145                 150                 155                 160

Asn Leu Pro Lys Ser Leu Ala Glu Leu Arg Ile His Asp Asn Lys Val
                165                 170                 175

Lys Lys Ile Gln Lys Asp Thr Phe Lys Gly Met Asn Ala Leu His Val
            180                 185                 190

Leu Glu Met Ser Ala Asn Pro Leu Glu Asn Asn Gly Ile Glu Pro Gly
        195                 200                 205

Ala Phe Glu Gly Val Thr Val Phe His Ile Arg Ile Ala Glu Ala Lys
    210                 215                 220

Leu Thr Ser Ile Pro Lys Gly Leu Pro Pro Thr Leu Leu Glu Leu His
225                 230                 235                 240

Leu Asp Phe Asn Lys Ile Ser Thr Val Glu Leu Glu Asp Leu Lys Arg
                245                 250                 255

Tyr Arg Glu Leu Gln Arg Leu Gly Leu Gly Asn Asn Arg Ile Thr Asp
            260                 265                 270

Ile Glu Asn Gly Thr Phe Ala Asn Ile Pro Arg Val Arg Glu Ile His
        275                 280                 285

Leu Glu His Asn Lys Leu Lys Lys Ile Pro Ser Gly Leu Gln Glu Leu
    290                 295                 300

Lys Tyr Leu Gln Ile Ile Phe Leu His Tyr Asn Ser Ile Ala Lys Val
305                 310                 315                 320

Gly Val Asn Asp Phe Cys Pro Thr Val Pro Lys Met Lys Lys Ser Leu
                325                 330                 335

Tyr Ser Ala Ile Ser Leu Phe Asn Asn Pro Met Lys Tyr Trp Glu Ile
            340                 345                 350

Gln Pro Ala Thr Phe Arg Cys Val Leu Gly Arg Met Ser Val Gln Leu
        355                 360                 365

Gly Asn Val Gly Lys
        370

<210> SEQ ID NO 7
<211> LENGTH: 14
<212> TYPE: PRT
```

-continued

<213> ORGANISM: Mus musculus

<400> SEQUENCE: 7

Asp Met Glu Asp Thr Asp Asp Asp Asn Asp Asp Asp
1               5                   10

<210> SEQ ID NO 8
<211> LENGTH: 10
<212> TYPE: PRT
<213> ORGANISM: Mus musculus

<400> SEQUENCE: 8

Arg Met Val Asp Leu Gln Asn Asn Lys Ile
1               5                   10

<210> SEQ ID NO 9
<211> LENGTH: 11
<212> TYPE: PRT
<213> ORGANISM: Mus musculus

<400> SEQUENCE: 9

Leu Tyr Ala Leu Ile Leu Asn Asn Asn Lys Leu
1               5                   10

<210> SEQ ID NO 10
<211> LENGTH: 12
<212> TYPE: PRT
<213> ORGANISM: Mus musculus

<400> SEQUENCE: 10

Lys Leu Arg Arg Leu Tyr Leu Ser His Asn Gln Leu
1               5                   10

<210> SEQ ID NO 11
<211> LENGTH: 12
<212> TYPE: PRT
<213> ORGANISM: Mus musculus

<400> SEQUENCE: 11

Ser Leu Ala Glu Leu Arg Ile His Asp Asn Lys Val
1               5                   10

<210> SEQ ID NO 12
<211> LENGTH: 12
<212> TYPE: PRT
<213> ORGANISM: Mus musculus

<400> SEQUENCE: 12

Ala Leu His Val Leu Glu Met Ser Ala Asn Pro Leu
1               5                   10

<210> SEQ ID NO 13
<211> LENGTH: 12
<212> TYPE: PRT
<213> ORGANISM: Mus musculus

<400> SEQUENCE: 13

Thr Val Phe His Ile Arg Ile Ala Glu Ala Lys Leu
1               5                   10

<210> SEQ ID NO 14
<211> LENGTH: 12
<212> TYPE: PRT
<213> ORGANISM: Mus musculus

```
<400> SEQUENCE: 14

Thr Leu Leu Glu Leu His Leu Asp Phe Asn Lys Ile
1               5                   10

<210> SEQ ID NO 15
<211> LENGTH: 12
<212> TYPE: PRT
<213> ORGANISM: Mus musculus

<400> SEQUENCE: 15

Glu Leu Gln Arg Leu Gly Leu Gly Asn Asn Arg Ile
1               5                   10

<210> SEQ ID NO 16
<211> LENGTH: 12
<212> TYPE: PRT
<213> ORGANISM: Mus musculus

<400> SEQUENCE: 16

Arg Val Arg Glu Ile His Leu Glu His Asn Lys Leu
1               5                   10

<210> SEQ ID NO 17
<211> LENGTH: 12
<212> TYPE: PRT
<213> ORGANISM: Mus musculus

<400> SEQUENCE: 17

Tyr Leu Gln Ile Ile Phe Leu His Tyr Asn Ser Ile
1               5                   10

<210> SEQ ID NO 18
<211> LENGTH: 380
<212> TYPE: PRT
<213> ORGANISM: Homo sapiens

<400> SEQUENCE: 18

Met Lys Glu Tyr Val Leu Leu Leu Phe Leu Ala Leu Cys Ser Ala Lys
1               5                   10                  15

Pro Phe Phe Ser Pro Ser His Ile Ala Leu Lys Asn Met Met Leu Lys
                20                  25                  30

Asp Met Glu Asp Thr Asp Asp Asp Asp Asp Asp Asp Asp Asp Asp Asp
            35                  40                  45

Asp Asp Asp Glu Asp Asn Ser Leu Phe Pro Thr Arg Glu Pro Arg Ser
        50                  55                  60

His Phe Phe Pro Phe Asp Leu Phe Pro Met Cys Pro Phe Gly Cys Gln
65                  70                  75                  80

Cys Tyr Ser Arg Val Val His Cys Ser Asp Leu Gly Leu Thr Ser Val
                85                  90                  95

Pro Thr Asn Ile Pro Phe Asp Thr Arg Met Leu Asp Leu Gln Asn Asn
                100                 105                 110

Lys Ile Lys Glu Ile Lys Glu Asn Asp Phe Lys Gly Leu Thr Ser Leu
            115                 120                 125

Tyr Gly Leu Ile Leu Asn Asn Asn Lys Leu Thr Lys Ile His Pro Lys
        130                 135                 140

Ala Phe Leu Thr Thr Lys Lys Leu Arg Arg Leu Tyr Leu Ser His Asn
145                 150                 155                 160

Gln Leu Ser Glu Ile Pro Leu Asn Leu Pro Lys Ser Leu Ala Glu Leu
                165                 170                 175
```

```
Arg Ile His Glu Asn Lys Val Lys Ile Gln Lys Asp Thr Phe Lys
            180                 185                 190

Gly Met Asn Ala Leu His Val Leu Glu Met Ser Ala Asn Pro Leu Asp
                195                 200                 205

Asn Asn Gly Ile Glu Pro Gly Ala Phe Glu Gly Val Thr Val Phe His
            210                 215                 220

Ile Arg Ile Ala Glu Ala Lys Leu Thr Ser Val Pro Lys Gly Leu Pro
225                 230                 235                 240

Pro Thr Leu Leu Glu Leu His Leu Asp Tyr Asn Lys Ile Ser Thr Val
                245                 250                 255

Glu Leu Glu Asp Phe Lys Arg Tyr Lys Glu Leu Gln Arg Leu Gly Leu
                260                 265                 270

Gly Asn Asn Lys Ile Thr Asp Ile Glu Asn Gly Ser Leu Ala Asn Ile
                275                 280                 285

Pro Arg Val Arg Glu Ile His Leu Glu Asn Asn Lys Leu Lys Lys Ile
            290                 295                 300

Pro Ser Gly Leu Pro Glu Leu Lys Tyr Leu Gln Ile Ile Phe Leu His
305                 310                 315                 320

Ser Asn Ser Ile Ala Arg Val Gly Val Asn Asp Phe Cys Pro Thr Val
                325                 330                 335

Pro Lys Met Lys Lys Ser Leu Tyr Ser Ala Ile Ser Leu Phe Asn Asn
                340                 345                 350

Pro Val Lys Tyr Trp Glu Met Gln Pro Ala Thr Phe Arg Cys Val Leu
                355                 360                 365

Ser Arg Met Ser Val Gln Leu Gly Asn Phe Gly Met
370                 375                 380

<210> SEQ ID NO 19
<211> LENGTH: 369
<212> TYPE: PRT
<213> ORGANISM: Mus musculus

<400> SEQUENCE: 19

Met Cys Pro Leu Trp Leu Leu Thr Leu Leu Ala Leu Ser Gln Ala
1               5                   10                  15

Leu Pro Phe Glu Gln Lys Gly Phe Trp Asp Phe Thr Leu Asp Asp Gly
                20                  25                  30

Leu Leu Met Met Asn Asp Glu Glu Ala Ser Gly Ser Asp Thr Thr Ser
            35                  40                  45

Gly Val Pro Asp Leu Asp Ser Val Thr Pro Thr Phe Ser Ala Met Cys
        50                  55                  60

Pro Phe Gly Cys His Cys His Leu Arg Val Val Gln Cys Ser Asp Leu
65                  70                  75                  80

Gly Leu Lys Thr Val Pro Lys Glu Ile Ser Pro Asp Thr Thr Leu Leu
                85                  90                  95

Asp Leu Gln Asn Asn Asp Ile Ser Glu Leu Arg Lys Asp Asp Phe Lys
            100                 105                 110

Gly Leu Gln His Leu Tyr Ala Leu Val Leu Val Asn Asn Lys Ile Ser
        115                 120                 125

Lys Ile His Glu Lys Ala Phe Ser Pro Leu Arg Lys Leu Gln Lys Leu
    130                 135                 140

Tyr Ile Ser Lys Asn His Leu Val Glu Ile Pro Pro Asn Leu Pro Ser
145                 150                 155                 160

Ser Leu Val Glu Leu Arg Ile His Asp Asn Arg Ile Arg Lys Val Pro
                165                 170                 175
```

```
Lys Gly Val Phe Ser Gly Leu Arg Asn Met Asn Cys Ile Glu Met Gly
            180                 185                 190

Gly Asn Pro Leu Glu Asn Ser Gly Phe Glu Pro Gly Ala Phe Asp Gly
            195                 200                 205

Leu Lys Leu Asn Tyr Leu Arg Ile Ser Glu Ala Lys Leu Thr Gly Ile
            210                 215                 220

Pro Lys Asp Leu Pro Glu Thr Leu Asn Glu Leu His Leu Asp His Asn
225                 230                 235                 240

Lys Ile Gln Ala Ile Glu Leu Glu Asp Leu Leu Arg Tyr Ser Lys Leu
                245                 250                 255

Tyr Arg Leu Gly Leu Gly His Asn Gln Ile Arg Met Ile Glu Asn Gly
            260                 265                 270

Ser Leu Ser Phe Leu Pro Thr Leu Arg Glu Leu His Leu Asp Asn Asn
            275                 280                 285

Lys Leu Ser Arg Val Pro Ala Gly Leu Pro Asp Leu Lys Leu Leu Gln
            290                 295                 300

Val Val Tyr Leu His Ser Asn Asn Ile Thr Lys Val Gly Ile Asn Asp
305                 310                 315                 320

Phe Cys Pro Met Gly Phe Gly Val Lys Arg Ala Tyr Tyr Asn Gly Ile
                325                 330                 335

Ser Leu Phe Asn Asn Pro Val Pro Tyr Trp Glu Val Gln Pro Ala Thr
            340                 345                 350

Phe Arg Cys Val Thr Asp Arg Leu Ala Ile Gln Phe Gly Asn Tyr Lys
            355                 360                 365

Lys

<210> SEQ ID NO 20
<211> LENGTH: 354
<212> TYPE: PRT
<213> ORGANISM: Mus musculus

<400> SEQUENCE: 20

Met Lys Ala Thr Leu Ile Phe Phe Leu Leu Ala Gln Val Ser Trp Ala
1               5                   10                  15

Gly Pro Phe Glu Gln Arg Gly Leu Phe Asp Phe Met Leu Glu Asp Glu
            20                  25                  30

Ala Ser Gly Ile Ile Pro Tyr Asp Pro Asp Asn Pro Leu Ile Ser Met
            35                  40                  45

Cys Pro Tyr Arg Cys Gln Cys His Leu Arg Val Val Gln Cys Ser Asp
        50                  55                  60

Leu Gly Leu Asp Lys Val Pro Trp Asp Phe Pro Pro Asp Thr Thr Leu
65                  70                  75                  80

Leu Asp Leu Gln Asn Asn Lys Ile Thr Glu Ile Lys Glu Gly Ala Phe
                85                  90                  95

Lys Asn Leu Lys Asp Leu His Thr Leu Ile Leu Val Asn Asn Lys Ile
            100                 105                 110

Ser Lys Ile Ser Pro Glu Ala Phe Lys Pro Leu Val Lys Leu Glu Arg
            115                 120                 125

Leu Tyr Leu Ser Lys Asn Gln Leu Lys Glu Leu Pro Glu Lys Met Pro
        130                 135                 140

Arg Thr Leu Gln Glu Leu Arg Val His Glu Asn Glu Ile Thr Lys Leu
145                 150                 155                 160

Arg Lys Ser Asp Phe Asn Gly Leu Asn Asn Val Leu Val Ile Glu Leu
                165                 170                 175
```

```
Gly Gly Asn Pro Leu Lys Asn Ser Gly Ile Glu Asn Gly Ala Phe Gln
            180                 185                 190
Gly Leu Lys Ser Leu Ser Tyr Ile Arg Ile Ser Asp Thr Asn Ile Thr
        195                 200                 205
Ala Ile Pro Gln Gly Leu Pro Thr Ser Leu Thr Glu Val His Leu Asp
    210                 215                 220
Gly Asn Lys Ile Thr Lys Val Asp Ala Pro Ser Leu Lys Gly Leu Ile
225                 230                 235                 240
Asn Leu Ser Lys Leu Gly Leu Ser Phe Asn Ser Ile Thr Val Met Glu
            245                 250                 255
Asn Gly Ser Leu Ala Asn Val Pro His Leu Arg Glu Leu His Leu Asp
            260                 265                 270
Asn Asn Lys Leu Leu Arg Val Pro Ala Gly Leu Ala Gln His Lys Tyr
        275                 280                 285
Ile Gln Val Val Tyr Leu His Asn Asn Asn Ile Ser Ala Val Gly Gln
    290                 295                 300
Asn Asp Phe Cys Arg Ala Gly His Pro Ser Arg Lys Ala Ser Tyr Ser
305                 310                 315                 320
Ala Val Ser Leu Tyr Gly Asn Pro Val Arg Tyr Trp Glu Ile Phe Pro
            325                 330                 335
Asn Thr Phe Arg Cys Val Tyr Val Arg Ser Ala Ile Gln Leu Gly Asn
            340                 345                 350
Tyr Lys

<210> SEQ ID NO 21
<211> LENGTH: 15
<212> TYPE: PRT
<213> ORGANISM: Mus musculus

<400> SEQUENCE: 21

Met Lys Glu Tyr Val Met Leu Leu Leu Ala Val Cys Ser Ala
1               5                   10                  15

<210> SEQ ID NO 22
<211> LENGTH: 358
<212> TYPE: PRT
<213> ORGANISM: Mus musculus

<400> SEQUENCE: 22

Lys Pro Phe Phe Ser Pro Ser His Thr Ala Leu Lys Asn Met Met Leu
1               5                   10                  15
Lys Asp Met Glu Asp Thr Asp Asp Asp Asn Asp Asp Asp Asn
            20                  25                  30
Ser Leu Phe Pro Thr Lys Glu Pro Val Asn Pro Phe Pro Phe Asp
        35                  40                  45
Leu Phe Pro Thr Cys Pro Phe Gly Cys Gln Cys Tyr Ser Arg Val Val
    50                  55                  60
His Cys Ser Asp Leu Gly Leu Thr Ser Val Pro Asn Asn Ile Pro Phe
65                  70                  75                  80
Asp Thr Arg Met Val Asp Leu Gln Asn Asn Lys Ile Lys Glu Ile Lys
            85                  90                  95
Glu Asn Asp Phe Lys Gly Leu Thr Ser Leu Tyr Ala Leu Ile Leu Asn
            100                 105                 110
Asn Asn Lys Leu Thr Lys Ile His Pro Lys Thr Phe Leu Thr Thr Lys
        115                 120                 125
```

```
Lys Leu Arg Arg Leu Tyr Leu Ser His Asn Gln Leu Ser Glu Ile Pro
            130                 135                 140
Leu Asn Leu Pro Lys Ser Leu Ala Glu Leu Arg Ile His Asp Asn Lys
145                 150                 155                 160
Val Lys Lys Ile Gln Lys Asp Thr Phe Lys Gly Met Asn Ala Leu His
                165                 170                 175
Val Leu Glu Met Ser Ala Asn Pro Leu Glu Asn Asn Gly Ile Glu Pro
            180                 185                 190
Gly Ala Phe Glu Gly Val Thr Val Phe His Ile Arg Ile Ala Glu Ala
                195                 200                 205
Lys Leu Thr Ser Ile Pro Lys Gly Leu Pro Pro Thr Leu Leu Glu Leu
            210                 215                 220
His Leu Asp Phe Asn Lys Ile Ser Thr Val Glu Leu Glu Asp Leu Lys
225                 230                 235                 240
Arg Tyr Arg Glu Leu Gln Arg Leu Gly Leu Gly Asn Asn Arg Ile Thr
                245                 250                 255
Asp Ile Glu Asn Gly Thr Phe Ala Asn Ile Pro Arg Val Arg Glu Ile
                260                 265                 270
His Leu Glu His Asn Lys Leu Lys Lys Ile Pro Ser Gly Leu Gln Glu
            275                 280                 285
Leu Lys Tyr Leu Gln Ile Ile Phe Leu His Tyr Asn Ser Ile Ala Lys
            290                 295                 300
Val Gly Val Asn Asp Phe Cys Pro Thr Val Pro Lys Met Lys Lys Ser
305                 310                 315                 320
Leu Tyr Ser Ala Ile Ser Leu Phe Asn Asn Pro Met Lys Tyr Trp Glu
                325                 330                 335
Ile Gln Pro Ala Thr Phe Arg Cys Val Leu Gly Arg Met Ser Val Gln
                340                 345                 350
Leu Gly Asn Val Gly Lys
            355

<210> SEQ ID NO 23
<211> LENGTH: 14
<212> TYPE: PRT
<213> ORGANISM: Mus musculus
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(13)
<223> OTHER INFORMATION: Xaa can be any naturally occurring amino acid

<400> SEQUENCE: 23

Cys Xaa Xaa Xaa Cys Xaa Cys Xaa Xaa Xaa Xaa Xaa Xaa Cys
1               5                   10

<210> SEQ ID NO 24
<211> LENGTH: 17
<212> TYPE: PRT
<213> ORGANISM: Mus musculus
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
```

```
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(16)
<223> OTHER INFORMATION: Xaa can be any naturally occurring amino acid

<400> SEQUENCE: 24

Cys Xaa Xaa Xaa Cys Xaa Cys Xaa Xaa Xaa Xaa Xaa Xaa Xaa Xaa
1               5                   10                  15

Cys

<210> SEQ ID NO 25
<211> LENGTH: 13
<212> TYPE: PRT
<213> ORGANISM: Mus musculus
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(12)
<223> OTHER INFORMATION: Xaa can be any naturally occurring amino acid

<400> SEQUENCE: 25

Cys Xaa Xaa Cys Xaa Cys Xaa Xaa Xaa Xaa Xaa Xaa Cys
1               5                   10

<210> SEQ ID NO 26
<211> LENGTH: 12
<212> TYPE: PRT
<213> ORGANISM: Mus musculus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa is Leu or Ile
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: MISC_FEATURE
<222> LOCATION: (12)..(12)
<223> OTHER INFORMATION: Xaa is Leu or Ile

<400> SEQUENCE: 26

Xaa Leu Xaa Xaa Leu Xaa Xaa Xaa Xaa Asn Xaa Xaa
1               5                   10

<210> SEQ ID NO 27
<211> LENGTH: 30
```

```
<212> TYPE: DNA
<213> ORGANISM: Mus musculus

<400> SEQUENCE: 27
aggcttcact ggctctttcg taggaaaaag                                        30

<210> SEQ ID NO 28
<211> LENGTH: 29
<212> TYPE: DNA
<213> ORGANISM: Mus musculus

<400> SEQUENCE: 28
cgtcatcatc tgtgtcttcc atatccttc                                         29

<210> SEQ ID NO 29
<211> LENGTH: 31
<212> TYPE: DNA
<213> ORGANISM: Mus musculus

<400> SEQUENCE: 29
cttgaagatc ttaaacggta cagggaactg c                                      31

<210> SEQ ID NO 30
<211> LENGTH: 30
<212> TYPE: DNA
<213> ORGANISM: Mus musculus

<400> SEQUENCE: 30
ccacgtgtga gagagataca cttggaacac                                        30

<210> SEQ ID NO 31
<211> LENGTH: 33
<212> TYPE: DNA
<213> ORGANISM: Mus musculus

<400> SEQUENCE: 31
cgcggatcca aaccttcttt tagcccttcc cac                                    33

<210> SEQ ID NO 32
<211> LENGTH: 33
<212> TYPE: DNA
<213> ORGANISM: Mus musculus

<400> SEQUENCE: 32
cgcggatcct tattttccaa cattcccaag ctg                                    33

<210> SEQ ID NO 33
<211> LENGTH: 24
<212> TYPE: DNA
<213> ORGANISM: Mus musculus

<400> SEQUENCE: 33
ggacacgttc aagggaatga atgc                                              24

<210> SEQ ID NO 34
<211> LENGTH: 36
<212> TYPE: DNA
<213> ORGANISM: Homo sapiens

<400> SEQUENCE: 34
ccgctcgagt tacattccaa agttcccaag ctgaac                                 36

<210> SEQ ID NO 35
```

```
<211> LENGTH: 30
<212> TYPE: DNA
<213> ORGANISM: Homo sapiens

<400> SEQUENCE: 35
actgcaatag atgcttgttt ctctcaaccc                                      30

<210> SEQ ID NO 36
<211> LENGTH: 28
<212> TYPE: DNA
<213> ORGANISM: Mus musculus

<400> SEQUENCE: 36
cctgagaccc tgaacgaact tcacctgg                                        28

<210> SEQ ID NO 37
<211> LENGTH: 29
<212> TYPE: DNA
<213> ORGANISM: Mus musculus

<400> SEQUENCE: 37
cggtggcagt gtgctctatc catctttcc                                       29

<210> SEQ ID NO 38
<211> LENGTH: 27
<212> TYPE: DNA
<213> ORGANISM: Mus musculus

<400> SEQUENCE: 38
gcacatagag gctgttagga gggctgg                                         27

<210> SEQ ID NO 39
<211> LENGTH: 29
<212> TYPE: DNA
<213> ORGANISM: Mus musculus

<400> SEQUENCE: 39
cgtcatcatc tgtgtcttcc atatccttc                                       29

<210> SEQ ID NO 40
<211> LENGTH: 33
<212> TYPE: DNA
<213> ORGANISM: Mus musculus

<400> SEQUENCE: 40
cgcggatcca aaccttctt tagcccttcc cac                                   33

<210> SEQ ID NO 41
<211> LENGTH: 31
<212> TYPE: DNA
<213> ORGANISM: Mus musculus

<400> SEQUENCE: 41
cgagtatcaa atggaatgtt gtttggaacc g                                    31

<210> SEQ ID NO 42
<211> LENGTH: 31
<212> TYPE: DNA
<213> ORGANISM: Mus musculus

<400> SEQUENCE: 42
gcgttccaaa caacattcca tttgatactc g                                    31
```

```
<210> SEQ ID NO 43
<211> LENGTH: 29
<212> TYPE: DNA
<213> ORGANISM: Mus musculus

<400> SEQUENCE: 43
gttggttgtg ggataaatat agccttctc                                    29

<210> SEQ ID NO 44
<211> LENGTH: 29
<212> TYPE: DNA
<213> ORGANISM: Mus musculus

<400> SEQUENCE: 44
gagaaggcta tatttatccc acaaccaac                                    29

<210> SEQ ID NO 45
<211> LENGTH: 30
<212> TYPE: DNA
<213> ORGANISM: Mus musculus

<400> SEQUENCE: 45
ccctggttct atcccgttgt tctcaagagg                                   30

<210> SEQ ID NO 46
<211> LENGTH: 30
<212> TYPE: DNA
<213> ORGANISM: Mus musculus

<400> SEQUENCE: 46
cctcttgaga acaacgggat agaaccaggg                                   30

<210> SEQ ID NO 47
<211> LENGTH: 29
<212> TYPE: DNA
<213> ORGANISM: Mus musculus

<400> SEQUENCE: 47
ctttgcagtt ccctgtaccg tttaagatc                                    29

<210> SEQ ID NO 48
<211> LENGTH: 31
<212> TYPE: DNA
<213> ORGANISM: Mus musculus

<400> SEQUENCE: 48
cttgaagatc ttaaacggta cagggaactg c                                 31

<210> SEQ ID NO 49
<211> LENGTH: 30
<212> TYPE: DNA
<213> ORGANISM: Mus musculus

<400> SEQUENCE: 49
gagttccaag tgtatctctc tcacacgtgg                                   30

<210> SEQ ID NO 50
<211> LENGTH: 30
<212> TYPE: DNA
<213> ORGANISM: Mus musculus

<400> SEQUENCE: 50
ccacgtgtga gagagataca cttggaacac                                   30
```

-continued

```
<210> SEQ ID NO 51
<211> LENGTH: 33
<212> TYPE: DNA
<213> ORGANISM: Mus musculus

<400> SEQUENCE: 51
cgcggatcct tattttccaa cattcccaag ctg                                33
```

NUCLEOTIDE AND AMINO ACID SEQUENCES OF ASPORINS

CROSS REFERENCE TO RELATED APPLICATIONS

The present application claims priority to U.S. Provisional Patent Application Ser. No. 60/341,537 filed Dec. 13, 2001, the contents of all of which are incorporated herein by reference.

FIELD OF THE INVENTION

The invention relates generally to small leucine rich repeat proteoglycan family proteins, nucleic acids encoding them, and methods for their use.

BACKGROUND OF THE INVENTION

The small leucine rich repeat proteoglycans (or SLRPs) are a group of extracellular proteins (ECM) that belong to the leucine-rich repeat (LRR) superfamily of proteins (Iozzo, R. V., and Murdoch, A. D. (1996) Faseb J. 10(5), 598-614; Hocking, A., et al. (1998) Matrix Biology 17, 1-19). The LRR is a protein folding motif composed of 20-30 amino acids with leucines in conserved positions. LRR-containing proteins are present in a broad spectrum of organisms and possess diverse cellular functions and localization (Kobe, B., and Deisenhofer, J. (1994) Trends in Biochemical Sciences, 415-421). The members of the SLRP subfamily have core proteins of similar size (about 40 kilodaltons) that are dominated by a central domain composed of 6-10 tandemly repeated LRRs. This domain is flanked by smaller, less conserved N-terminal and C-terminal regions containing cysteines in characteristic positions.

Most of the SLRP proteins are proteoglycans, and the SLRP gene family has been subdivided into 3 classes based on similarities in overall amino acid sequence, spacing of cysteine residues in the N-terminus, and gene structure. The previously identified class I members, decorin (Krusius, T., and Ruoslahti, E. (1986) Proc. Natl. Acad. Sci. U.S.A. 83(20), 7683-7) and biglycan (Fisher, L. W., et al. (1989) J. Biol. Chem. 264(8), 4571-4576), are the closest related SLRPs based on amino acid sequences; the human sequences are 57% identical. The N-terminal regions of decorin and biglycan are substituted with one and two chondroitin/dermatan-sulfate chains, respectively. The cysteine-rich cluster in the N-terminus of class I SLRPs has an amino acid spacing of $CX_3CXCX_6C$ (SEQ ID NO:23). The mouse decorin (Scholzen, T., et al. (1994) J. Biol. Chem. 269(45), 28270-81) and biglycan genes (Wegrowski, Y., et al. (1995) Genomics 30(1), 8-17) contain 8 exons.

Class II members, fibromodulin (Oldberg, A., et al. (1989) EMBO 8(9), 2601-2604), lumican (Blochberger, T., et al. (1992) J. Chem. 267(1), 347-352), PRELP (Bengtsson, E., et al. (1995) J. Biol. Chem. 270(43), 25639-25644), keratocan (Corpuz, L. M., et al. (1996) J. Biol. Chem. 271(16), 9759-63), and osteoadherin (Sommarin, Y., et al. (1998) J. Biol. Chem. 273(27), 16723-9), have a pairwise amino acid sequence identity ranging between 37-55% and have a common gene structure composed of three exons. The cysteine spacing in the N-terminal region of class II SLRPs is identical ($CX_3CXCX_9C$ (SEQ ID NO:24)) but different from the other SLRP classes. The core proteins of class II SLRPs (with the exception of PRFLP) can be substituted with N-linked keratan sulfate glycosaminoglycan chain(s).

The class III members, epiphycan/PG-Lb (Shinomura, T., and Kimata, K. (1992) J. Biol. Chem. 267(2), 1265-1270; Johnson, H. J., et al. (1997) J. Biol. Chem. 272, 18709-18717), osteoglycin/mimecan (Madisen, L., et al. (1990) DNA Cell. Biol. 9(5), 303-309; Funderburgh, J. L., et al. (1997) J. Biol. Chem. 272(44), 28089-28095), and opticin (Reardon, A. J., et al. (2000) J. Biol. Chem. 275(3), 2123-2129), have a pairwise amino acid sequence identity ranging between 35-42% and have a common gene structure composed of either 7 or 8 exons. Class III SLRPs contain only 6 LRRs, and the cysteine spacing in the N-terminal region of class III SLRPs is unique ($CX_2CXCX_6C$ (SEQ ID NO:25)). The recently identified opticin is substituted with O-linked sialylated oligosaccharides, and consequently is a glycoprotein rather than a proteoglycan. On the other hand, osteoglycin/mimecan and epiphycan can be substituted with N-linked keratan sulfate glycosaminoglycan chain(s) and O-linked chondroitin/dermatan sulfate chain(s), respectively. Interestingly, many of the SLRP proteoglycans have been isolated without attached glycosaminoglycans, suggesting that they are "part-time" proteoglycans (Grover, J., et al. (1995) J. Biol. Chem. 270(37), 21942-21949; Corpuz, L. M., et al. (1996) J. Biol. Chem. 271(16), 9759-9763; Funderburgh, J. L., et al. (1997) J. Biol. Chem. 272(44), 28089-28095).

Several SLRP proteins display potent effects in vitro. For example, recombinant decorin, biglycan, and fibromodulin bind to TGF-β in vitro (Hildebrand, A., et al. (1994) Biochem. J. 302, 527-534), and decorin can interfere with TGF-β dependent proliferation of Chinese hamster ovary (CHO) cells (Yamaguchi, Y., and Ruoslahti, E. (1988) Nature 336(6196), 244-246). Furthermore, injection of decorin into rats with experimental glomerulonephritis curtailed the abnormal deposition of matrix suggesting that decorin may affect TGF-β activity also in vivo (Border, W. A., and Ruoslahti, E. (1990) Cell Differ. Dev. 32(3), 425-431; Border, W. A., et al. (1992) Nature 360(6402), 361-364). Recently, it has been shown that decorin can down-regulate epidermal growth factor receptor (EGFR) leading to growth suppression, and decorin may act as a natural inhibitor of the EGFR signaling pathway (Csordas, G., et al. (2000) J. Biol. Chem. 275(42), 32879-32887).

The SLRPs have been shown to interact with a variety of extracellular matrix proteins, such as collagens (Gallagher, J. T., et al. (1983) Biochem. J. 215(1), 107-116), fibronectin (Schmidt, G., et al. (1987) J. Cell. Biol. 104(6), 1683-1691), and thrombospondin (Winnemoller, M., et al. (1992) Eur. J. Cell. Biol. 59(1), 47-55), as well as serum proteins, heparin cofactor II (Whinna, H. C., et al. (1993) J. Biol. Chem. 268(6), 3920-3924) and C1q (Krumdieck, R., et al. (1992) J. Immunol. 149(11), 3695-3701). Biochemical assays have demonstrated that decorin (Vogel, K. G., et al. (1984) Biochem. J. 223(3), 587-597), fibromodulin (Hedbom, E., and Heinegard, D. (1989) J. Biol. Chem. 264(12), 6898-6905), and lumican (Rada, J. A., et al. (1993) Exp. Eye Res. 56(6), 635-648) bind to collagens in vitro and modulate collagen fibril formation. Morphological analysis of mice "knockouts" demonstrates that decorin (Danielson, K. G., et al. (1997) J. Cell Biol. 136, 729-743), fibromodulin (Svensson, L., et al. (1999) J. Biol. Chem. 274(14), 9636-9647), and lumican (Chakravarti, S., et al. (1998) J. Cell. Biol. 141(5), 1277-1286), respectively, are necessary for normal collagen fibril formation in specialized connective tissues of skin, tendon, and cornea. Therefore, a role for SLRPs in collagen fiber formation is clearly established both in vivo and in vitro. Also, biglycan-null mice exhibit a mild osteoporosis-like phenotype (Xu, T., et al. (1998) Nat.

Genet. 20(1), 78-82). Recently, patients with cornea plana 2 (CNA2; MIM 217300) were shown to have mutations in the keratocan gene, a class II SLRP family member (Pellegata, N. S., et al. (2000) Nat. Genet. 25(1), 91-95).

Nucleotide sequencing of a human bacterial artificial chromosome (BAC, RPC111-91705), and contigs of overlapping BAC clones revealed that four SLRPs genes (decorin, lumican, keratocan, and epiphycan/PG-Lb) are physically linked on human chromosome 12q (Pellegata, N. S., et al. (2000) Nat. Genet. 25(1), 91-95). Previous genetic linkage studies in the mouse suggested that decorin, lumican, and epiphycan map together in a cluster in close proximity to the MgfX gene on mouse chromosome 10, and these genes are deleted in mice that have large deletion mutations at the Steel locus (Danielson, K. G., et al. (1999) Mamm. Genome 10(2), 201-203).

Despite the research performed to date, there still exists a need for an increased understanding of the molecular structure and function of the SLRP proteins. This understanding can be approached by further studies of the proteins themselves, their encoding nucleic acid sequences, and their interactions with other proteins and biological compounds in cellular systems.

SUMMARY OF THE INVENTION

A new member of the leucine-rich repeat (LRR) family of proteins is described from several tissues. It is a type I LRR closely related in amino acid sequence to decorin and biglycan. It is not, however, a proteoglycan but contains a unique stretch of aspartate residues and hence the name "asporin". The mouse genomic structure of asporin has been determined. The human and mouse chromosomal localization has also been determined. A vector has been constructed for the expression of recombinant asporin in the vaccinia virus system.

The functions of asporin are based on reported biological activities of decorin and biglycan. Because asporin is closely related to decorin and biglycan it is likely to have the same biological activities. Both decorin and biglycan molecules have been the subject of considerable research since they have the potent biological activities in vitro, and can (a) regulate the complement system, (b) inhibit fibrosis formation through manipulating the activation and/or activity of TGFβ and related molecules, (c) regulate growth of endothelial cells and angiogenesis, regulate the growth of cancer cells and in effect, shut down the growth of certain types of cancer and regulate the functions of neuromuscular junctions. Because asporin does not appear to be a proteoglycan, but possibly a glycoprotein, that is may be possible to solve its structure and use this molecule for rational drug design.

DESCRIPTION OF THE FIGURES

The following figures form part of the present specification and are included to further demonstrate certain aspects of the present invention. The invention may be better understood by reference to one or more of these figures in combination with the detailed description of specific embodiments presented herein.

| FIG. | Description |
|---|---|
| 1 | Full length mouse cDNA (2357 nt; SEQ ID NO:1). The open reading frame is 1122 nt in length (SEQ ID NO:2). The 5' untranslated region is 305 nt in length (SEQ ID NO:3), and the 3' untranslated region is 930 nt in length (SEQ ID NO:4). A non-canonical polyadenylation signal sequence of AATAA is found at positions 2326–2331 (SEQ ID NO:5). |
| 2 |
FIGS. 2A-2C show the CLUSTAL multiple protein sequence alignment of human asporin (SEQ ID NO:18), mouse asporin (SEQ ID NO:6), mouse biglycan (SEQ ID NO:19), and mouse decorin (SEQ ID NO:20). |
| 3 | Northern blots showing mRNA expression of class I SLRPs in mouse tissues. |
| 4 | RNA in situ hybridization using sagittal sections of mouse embryos.

DESCRIPTION OF THE SEQUENCE LISTINGS

Figure 3:
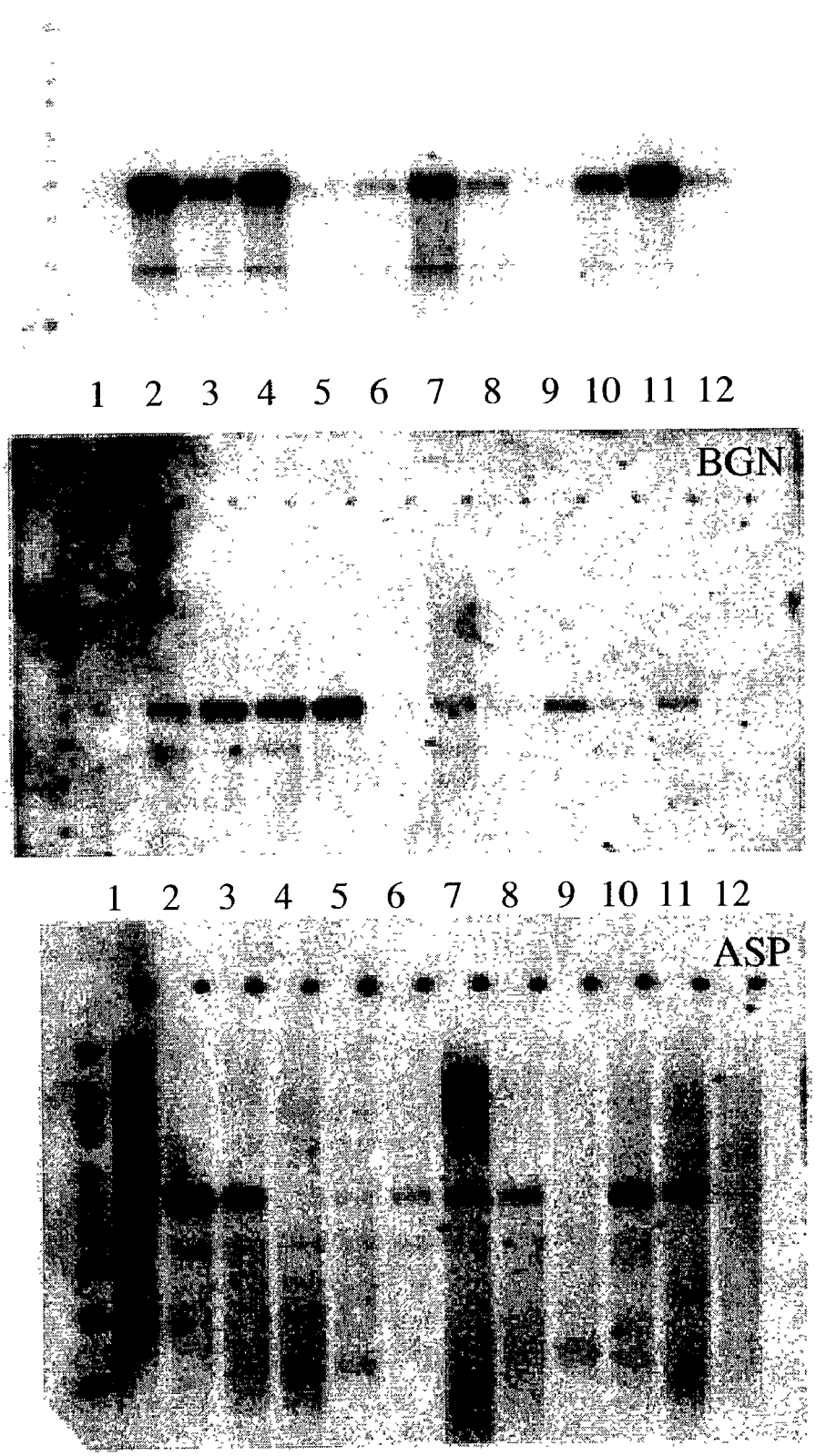

The following sequence listings form part of the present specification and are included to further demonstrate certain aspects of the present invention. The invention may be better understood by reference to one or more of these sequences in combination with the detailed description of specific embodiments presented herein.

| SEQ ID NO: | Description |
|---|---|
| 1 | Full length mouse asporin cDNA |
| 2 | Mouse asporin open reading frame |
| 3 | Mouse asporin 5' untranslated region |
| 4 | Mouse asporin 3' untranslated region |
| 5 | Polyadenylation signal sequence |
| 6 | Mouse full length encoded asporin protein |
| 7 | N-terminal acidic region of asporin protein |
| 8 | Leucine rich repeat #1 |
| 9 | Leucine rich repeat #2 |
| 10 | Leucine rich repeat #3 |
| 11 | Leucine rich repeat #4 |
| 12 | Leucine rich repeat #5 |
| 13 | Leucine rich repeat #6 |
| 14 | Leucine rich repeat #7 |
| 15 | Leucine rich repeat #8 |
| 16 | Leucine rich repeat #9 |
| 17 | Leucine rich repeat #10 |
| 18 | Human asporin protein |
| 19 | Mouse biglycan protein |
| 20 | Mouse decorin protein |
| 21 | Putative signal sequence |
| 22 | Mouse asporin sequence after cleavage of signal sequence |
| 23 | Cysteine cluster $CX_3CXCX_6C$ |
| 24 | Cysteine spacing in N-terminal region of class II SLRPs $CX_3CXCX_9C$ |
| 25 | Cysteine spacing in N-terminal region of class III SLRPs $CX_2CXCX_6C$ |
| 26 | Central consensus sequence X-L-X-X-L-X-L/I-X-X-N-X-L/I |
| 27 | Primer MS ASP RV 406 |
| 28 | Primer MS ASP RV 343 |
| 29 | Primer MS ASP FW 983 |
| 30 | Primer MS ASP FW 1077 |

-continued

| SEQ ID NO: | Description |
|---|---|
| 31 | Primer Ms Start FW |
| 32 | Primer Ms Stop RV |
| 33 | Primer MS FW 775 |
| 34 | Primer HU ASP RV STOP |
| 35 | Primer HU ASP RV 1503 |
| 36 | Primer MS BGN3 |
| 37 | Primer MS BGN4 |
| 38 | Primer Asp Ex 1 Fw38 |
| 39 | Primer Asp Ex 2 Rv343 |
| 40 | Primer Asp Ex 2 Start |
| 41 | Primer Asp Ex 3 Rv |
| 42 | Primer Asp Ex 3 Fw |
| 43 | Primer Asp Ex 4 Rv |
| 44 | Primer Asp Ex 4 Fw |
| 45 | Primer Asp Ex 5 Rv |
| 46 | Primer Asp Ex 5 Fw |
| 47 | Primer Asp Ex 6 Rv |
| 48 | Primer Asp Ex 6 Fw |
| 49 | Primer Asp Ex 7 Rv |
| 50 | Primer Asp Ex 7 Fw |
| 51 | Primer Asp Ex 8 Stop |

DETAILED DESCRIPTION OF THE INVENTION

Chromosomosomal localization of three other SLRPs, fibromodulin (Sztrolovics, R., et al. (1994) Genomics 23, 715-717), PRELP (Grover, J., et al. (1996) Genomics 38, 109-117), and opticin (Hobby, P., et al. (2000) Mol. Vis. 6, 72-78; Friedman, J. S., et al. (2000) Invest. Ophthalmol. Vis. Sci. 41(8), 2059-2066) to human chromosome 1q32 by fluorescent in situ hybridization (FISH) analysis and/or radiation hybrid mapping raised the possibility that these SLRP genes may also be physically linked. Under the presumption that additional unidentified SLRP gene(s) might be associated with these clusters or a yet unidentified cluster, a computer homology search of the genome databases was initiated to look for novel SLRP family members.

A novel SLRP family member that belongs to the class I subfamily and is closely related to biglycan and decorin is disclosed. This protein is named "asporin" due to the unique aspartate stretch at the N-terminus of the translated open reading frame. The molecular cloning of the full-length mouse and partial human cDNA and investigations of asporin mRNA expression in mouse embryonic development are disclosed. In addition, the mouse and human asporin gene structures have been determined, and it was discovered that the human asporin gene is part of a SLRP gene cluster on human chromosome 9q21.3-9q22 that also contains osteoadherin, osteoglycin/mimecan, and a gene encoding another LRR-containing protein, ECM2 (Nishiu, J., et al. (1998) Genomics 52(3), 378-381).

Recently, various GenBank submissions of asporin sequences have been made. AF316825 and AF316824 (Apr. 20, 2001; from Lorenzo, P. et al., *J. Biol. Chem.*, 276(15) 12201-12211, 2001) present the human and mouse DNA and deduced protein sequence. NM025711 (Jan. 7, 2002) and BC034888 (Sep. 20, 2002) have presented the mouse sequences, and NM017680 (Nov. 5, 2002) presented the human sequences. NW000075 (Nov. 17, 2002) presented the mouse sequence as part of a supercontig.

Asporin cDNA

A novel member of the class I SLRP gene family has been identified and named asporin. The cDNA sequence of human decorin (Krusius, T., and Ruoslahti, E. (1986) Proc. Natl. Acad. Sci. U.S.A. 83(20), 7683-7687) was submitted to GenBank as a query to search the human dbEST database using the BLAST-N algorithm. At the time, the nucleotide sequence of several human expressed sequence tags (ESTs: AK000136, FLJ20129, and AI539334) exhibited strong homology to the nucleotide sequence of the class I SLRPs. Since a computer generated "in frame" cDNA sequence could not be derived from overlapping ESTs, the human genomic sequence from bacterial artificial chromosome (BAC) AL137848 was used to correct the sequencing errors present in the human ESTs and to fill any gaps that were missing from the alignment of overlapping ESTs. These results revealed an open reading frame of 380 amino acids and were later confirmed experimentally by sequencing PCR products generated from 5' RACE reactions that used reverse transcribed human heart RNA (first-strand cDNA) as template. However, for the mouse, a computer generated "in frame" cDNA sequence of mouse asporin could not be obtained from overlapping ESTs thus leaving a gap in the computer derived open reading frame. Furthermore, the genomic sequence of mouse asporin was not available in the public databases. Therefore, oligonucleotide primers were designed from nucleotide sequences present in available 5' and 3' mouse ESTs, and a conventional PCR strategy was used to amplify a PCR fragment that "bridged the gap." The 5' and 3' cDNA ends of mouse asporin cDNA were determined by sequencing 5' and 3' RACE PCR products.

Consequently, a full length mouse cDNA of 2357 nucleotides was generated by aligning the nucleotide sequences of overlapping PCR reactions. Both the nucleotide sequence of the full length mouse cDNA as well as the translated open reading frame are shown in FIG. 1. The translated open reading frame encodes a protein of 373 amino acids that contains a putative signal peptide sequence of 15 amino acids predicted using the Signal P V1.1 program (the cleavage site is shown as an arrow). The central domain is composed of an array of 10 LRRs, and each LRR contains 24 amino acids with the central consensus sequence X-L-X-X-L-X-L/I-X-X-N-X-L/I (SEQ ID NO:26). The LRR domain is flanked by smaller cysteine containing N- and C-terminal regions. A cluster of four cysteines (C) in the N-terminal region conform to the amino acid spacing of $CX_3CXCX_6C$ (SEQ ID NO:23) that is also found in the other class I SLRP members. The C-terminal region contains two cysteines with 32 intervening amino acids, and this exact spacing is also found in decorin and biglycan. The only putative N-linked oligosaccharide attachment site is circled and is located between LRR#8 and LRR#9 as predicted by the NetOGlyc 2.0 program. Unlike decorin and biglycan, a serine/glycine dipeptide consensus sequences for O-linked oligosaccharide substitution is not present in the asporin ORF. Two cysteines in the C-terminus are boxed and are conserved amongst the SLRPs. A noncanonical polyadenylation signal sequence of AATAA (SEQ ID NO:5) in the 3' untranslated region of the mouse asporin cDNA is depicted in boldface, underlined letters.

In contrast to decorin and biglycan, a serine/glycine dipeptide consensus sequence for O-linked glycosaminoglycan substitution is not present in the translated open reading frame of asporin. One putative N-linked oligosaccharide attachment site, located between LRRs 8 and 9, can be found in the asporin ORF. A stretch of 14 amino acids N-terminal to the first cysteine cluster contains 10 aspartic acid residues. A similar stretch of acidic residues is not present in the other class I SLRPs, and hence the new member was named asporin.

The mouse asporin ORF (including the stop codon) is 1122 bp. The 5' untranslated and 3' untranslated regions of the mouse cDNA are 305 bp and 930 bp, respectively. A non-canonical polyadenylation signal sequence of AATAA (cDNA 2326-2331; SEQ ID NO:5) is present very close to the end of the 3' untranslated region of the mouse cDNA.

The transcriptional start site of the mouse asporin message was determined by 5' RACE using the SMART cDNA amplification kit. Several products of second round PCR amplification in the 5' RACE protocol were resolved electrophoretically on an ethidium bromide-stained 1% agarose gel. The products were not the same size suggesting that the mouse asporin gene may have multiple transcription start sites; however, this was not confirmed by another method (i.e. primer extension or ribonuclease protection assay). The largest 5' RACE PCR-amplified product was subcloned and was used as a probe for Northern hybridization, Southern hybridization, and RNA in situ hybridization experiments.

The transcription start site of human asporin, as well as the open reading frame and 5' untranslated region, were determined by nucleotide sequencing of 5' RACE products obtained with the SMART cDNA amplification kit. Several 5' RACE products were resolved electrophoretically on an ethidium bromide-stained 1% agarose gel. The products were subsequently cloned and sequenced.

Comparison of Human and Mouse Asporin ORFs with Decorin and Biglycan

The translated human asporin ORF was aligned with mouse asporin, mouse biglycan (Wegrowski, Y., et al. (1995) Genomics 30(1), 8-17), and mouse decorin (Scholzen, T., et al. (1994) J. Biol. Chem. 269(45), 28270-28281) ORFs using the CLUSTAL program (Identity) contained in the Macintosh MacVector software package (version 6.0.1) and is shown in FIGS. 2A-2B. The mouse and human asporin ORFs are 91% identical. The major difference is located in an acidic stretch in the N-terminal region of the translated human ORF (380 amino acids) that is 7 amino acids longer than the corresponding acidic stretch in the mouse ORF (373 amino acids), and hence accounts for the size difference between the two ORFs. The human ORF, like the mouse, also lacks a dipeptide serine/glycine consensus sequence for glycosaminoglycan substitution, but contains the same potential N-linked glycosylation substitution site located between the eighth and ninth LRR.

Multiple alignment of human asporin, mouse asporin, mouse biglycan, and mouse decorin open reading frames (ORFs) was performed with the CLUSTAL program (Identity) using the MacIntosh MacVector version 6.0.1 software. The human asporin ORF of 380 amino acids is 91% identical to the mouse asporin ORF of 373 amino acids. The acidic stretch at the N-terminus of human asporin (amino acids 33-53 of ORF) is 7 amino acids longer than the corresponding stretch in mouse asporin, and hence, accounts for the size difference between the two open reading frames. Neither the human nor the mouse asporin ORF contains a potential O-linked glycosaminoglycan substition site. However, both the human (asn #282) and mouse (asn #275) contain one potential N-linked glycosylation site. The amino acid identity between mouse asporin (373 a.a.) and mouse biglycan (369 a.a.) is 52% with an additional 17% similar residues. The amino acid identity between mouse asporin (373 a.a.) and mouse decorin (354 a.a.) is 49% with an additional 19% similar residues. The amino acid identity between mouse biglycan (369 a.a.) and mouse decorin (354 a.a.) is 54% with an additional 14% similar residues. Using the Clustal W (1.4) multiple alignment program, the number of identical amino acids shared by the three mouse aligned sequences is 141 amino acids.

The three mouse class I SLRPs have remarkably similar amino acid sequences. The translated ORF of mouse asporin (373 amino acids) is most homologous to that of mouse biglycan (369 amino acids) with 52% identical and an additional 17% similar residues. The amino acid identity between mouse asporin (373 amino acids) and mouse decorin (354 amino acids) is slightly less at 49% with an additional 19% similar residues. The amino acid identity between mouse biglycan (369 amino acids) and mouse decorin (354 amino acids) is 54% with an additional 14% similar residues. The region of lowest homology amongst the three mouse translated ORFs is N-terminal to the first cysteine cluster. The aspartate rich stretch of asporin is contained in this region, as is the serine residue(s) involved in O-linked glycosaminoglycan substitution of decorin and biglycan.

The mRNA expression for the class I SLRPs is broadly distributed in mammalian tissues (see FIG. 3). Three separate Northern hybridizations of a single mouse multi-tissue Northern blot using radiolabeled cDNA fragments of decorin (FIG. 3, top panel), biglycan (FIG. 3, center panel), and asporin (FIG. 3, bottom panel) were performed. The Northern results for mouse decorin (Scholzen, T., et al. (1994) J. Biol. Chem. 269(45), 28270-28281) and mouse biglycan (Wegrowski, Y., et al. (1995) Genomics 30(1), 8-17) confirm previously published work. The asporin probe recognized a single mRNA of 2.4 kb in the tissues tested. The asporin mRNA is comparable in size to the biglycan message of 2.4 kb and slightly larger than the decorin message of 1.8 kb.

Northern hybridization of a multiple tissue mouse poly A+ blot (Origene) of 12 tissues with 3 different random-labeled DNA probes (top panel, decorin; center panel, biglycan; bottom panel, asporin) were performed. The blot was commercially prepared so that it contains about 2 micrograms of poly A+ RNA per lane, and the tissues were taken from 9-10 month old Swiss Webster mice (thymus, 8-12 weeks old). The RNA was loaded in 12 lanes (left to right) from the following tissues: Brain(1), Heart(2), Kidney (3), Liver(4), Lung(5), Muscle(6), Skin(7), Small Intestine (8), Spleen(9), Stomach(10), Testis(11), and Thymus(12). Markers on the left side of the blot (dots representing Ambion RNA Millenium marker) from bottom to top are 0.5 kb, 1 kb, 1.5 kb, 2.0 kb, 2.5 kb, 3.0 kb, 4 kb, 5 kb, 6 kb, and 9 kb. The RNA message size of 1.8 kb for mouse decorin (6) and 2.4 kb for mouse biglycan (7) confirms previous reports. The mouse asporin message is about 2.4 kb.

For the 12 organs that were represented in the mouse adult multiple-tissue Northern blot, asporin message was most prominent in the heart. Asporin message was also detected in kidney, stomach, testes, and dermis but only weakly in lung, skeletal muscle, small intestine, and thymus. However, asporin message in brain, liver, and spleen was virtually undetectable at the longest exposure tested.

Similarities and differences in the relative RNA expression pattern of the three genes were found. A message for all three genes was detected in heart, kidney, skin, testes, and small intestine, but the message in brain was extremely weak for all the genes. Biglycan message in spleen and lung was fairly robust, yet asporin and decorin message were very weak in these organs. Asporin message was virtually undetectable in the liver, yet expression of biglycan and decorin mRNA expression were observed in this organ.

Expression of Asporin in Mouse Development

Figure 4:
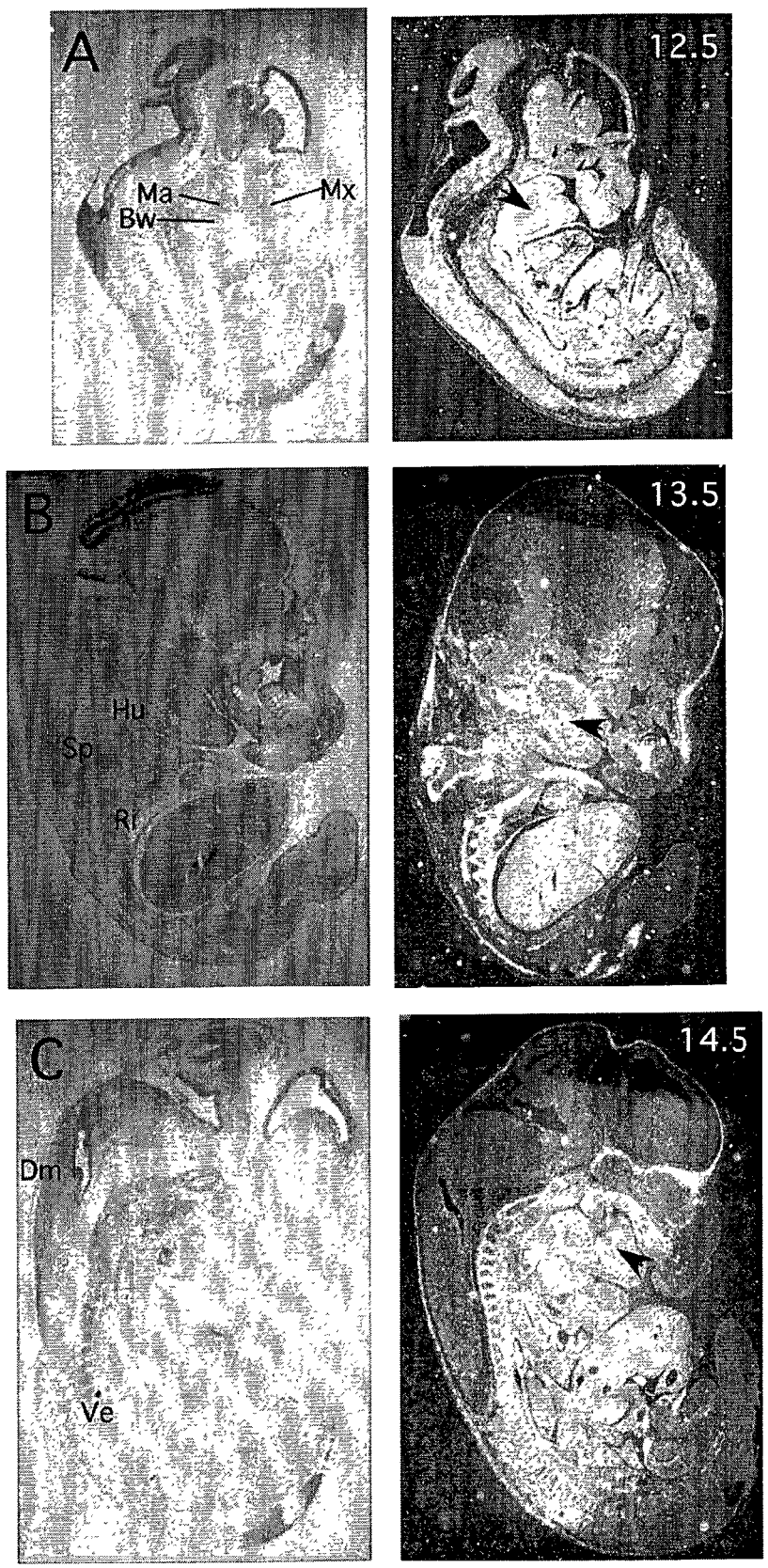
FIG. 4A is 12.5 dpc.
FIG. 4B is 13.5 dpc.
FIG. 4C is 14.5 dpc. |
| 5 |

The mouse multiple tissue Northern blot was used as a preliminary screen and did not include such tissues as bone and cartilage. Most importantly, the RNA expression pattern of asporin in specialized connective tissues can not be obtained by this method. Therefore, we embarked on a RNA in situ hybridization procedure using sagittal sections of mouse embryos at different stages of mouse development. No asporin mRNA was detected at the two earliest time points tested, 9.5 and 10.5 days post coitum (dpc) of mouse embryonic (ME) development. Asporin mRNA was detected at 12.5 dpc in the craniofacial regions of the maxilla and the mandible (FIG. 4).

Sagittal sections of mouse embryos at three different stages of development probed with an asporin anti-sense riboprobe. Dark field micrographs are shown to the right of the bright field images (magnification-1×). Top panels (A), at 12.5 dpc, asporin RNA is detected in the maxillary (Mx) and mandibular (Mn) components (arrow) of the first branchial arch and the thoracic body wall (Bw) adjacent to the heart. Middle panels (B), at 13.5 dpc, asporin is detected in the perichondrium of the scapula (Sp), ribs (Ri), and humerus (Hu). Asporin mRNA is not detected in Meckel's cartilage, but instead the mesenchymal cells lateral to Meckel's cartilage (shown with arrow). Bottom panels (C), at 14.5 dpc, asporin expression is detected in the perichondrium of the vertebrae (Ve). Condensing mesenchymal cells in the mandible surrounding Meckel's cartilage are positive for asporin RNA, and this cusp-like expression pattern is highlighted by the arrow. Strong expression of asporin is maintained in the mandible and maxilla, at future sites of intramembranous bone formation. Weak expression is also detected in the dermal mesenchyme (Dm) at 14.5 dpc.

At ME 12.5 dpc, a groove forms between the lower surface of the anterior tip of the tongue and the mandibular component of the first brachial arch. At this stage, asporin message is absent from the tongue, but is present in the mandibular (shown as an arrow in the 12.5 dpc panel) as well as maxillary components of the first branchial arch. The only other detectable signal in this section is present in the thoracic body wall adjacent to the heart and the umbilicus. Weak signal was also detected in the mesenchyme surrounding the central regions of the developing vertebrae (different section). At 12.5 dpc, asporin expression in the mandible may overlap with the precartilage condensations of the first branchial arch or Meckel's precartilage mass. Nevertheless, at ME 13.5 dpc, Meckel's cartilage is recognizable, and asporin mRNA expression is not detected in Meckel's cartilage, but instead is detected in the mesenchyme lateral to Meckel's cartilage. For this stage of development, the most pronounced expression of asporin is observed in the perichondrium of the humerus, ribs, and scapula. Strong expression was also detected in the body wall adjacent to the heart and the intercostal ligaments near the ribs. At ME 14.5 dpc, the mesenchymal condensations lateral to Meckel's cartilage are clearly positive, and the sagittal section of the mandible reveals that the asporin expression pattern appears as a "cusp" surrounding Meckel's cartilage. This "cusp-like" area will eventually ossify and give rise to intramembranous alveolar bone of the mandible. Asporin expression is also found in the perichondrium surrounding the central cartlaginous elements of the vertebrae. Weak asporin expression is detected in dermal mesenchyme.

Figure 5:
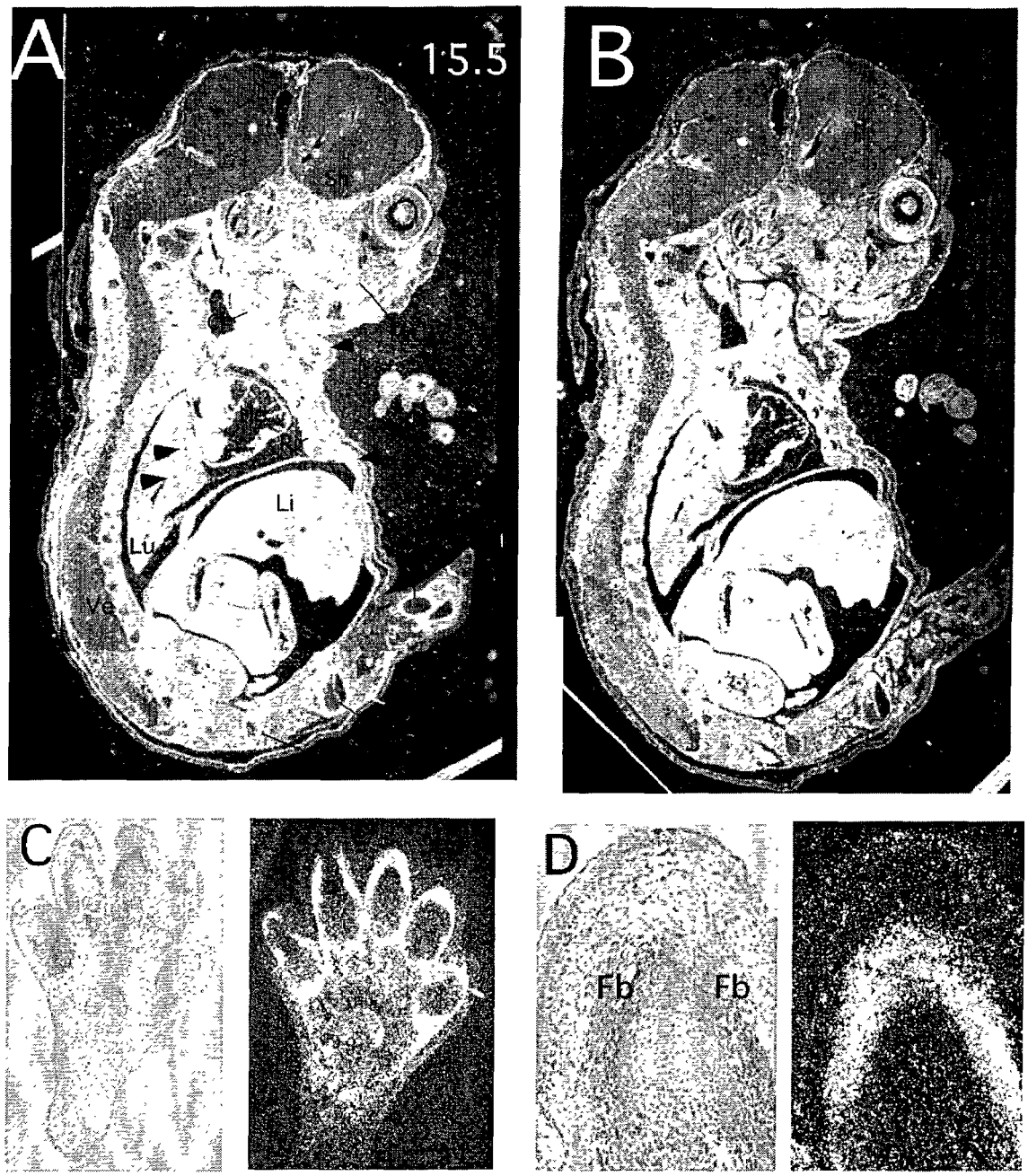
FIG. 5A is RNA in situ hybridization using sagittal sections of mouse embryos at 15.5 dpc.
FIG. 5B is a saggital section of the digits of the forelimb at 15.5 dpc.
FIG. 5C is a comparison of the dark and bright field micrographs of the distal end of the third digit.
FIG. 5D is a 20x magnification of FIG. 5C. |
| 6 |

FIG. 5 shows sagittal sections of a mouse embryo at 15.5 dpc probed with asporin sense and anti-sense riboprobes (magnification-1×). The section hybridized with the anti-sense riboprobe is shown at the top left (FIG. 5A), and a serial section that was hybridized with a "control" sense probe is shown at the top right (FIG. 5B). Asporin RNA is detected in the perichondrium/periosteum of the long bones such as the tibia (Ti), fibula (Fi), femur (Fe), iliac bone (Il), the flat bones at the base of the skull such as the sphenoid bone (Sh), ribs (Ri), clavicle (Cl) and vertebrae (Ve). Some of the intramembranous bones of the maxilla (Mx) and mandible (Mn) are also positive for asporin. A positive signal for asporin is detected in the region of the subcutaneous muscles of the thorax, trunk, and head (platysmal muscle), and these muscles are delineated with arrows. Very little asporin mRNA is detected in the major parenchymal organs, with the exception of the lung bronchi (arrow). A nonspecific signal is evident in the major parenchymal organs of heart (He), lung (Lu), and liver (Li) perhaps due to the nonspecific binding of the probe to the erythrocytes. A sagittal section of the digits from a forelimb at 15.5 dpc is shown in panel C (brightfield to left; darkfield to right; magnification of 4×). The tip of the third digit from FIG. 5C is shown in FIG. 5D (brightfield to left, darkfield to right; magnification of 20×). Asporin has a prominent expression in the fibroblast (Fb) layer of the perichondrium.

At ME 15.5 dpc (FIG. 5), sagittal sections reveal a robust expression of asporin in the perichondrium/periosteum of the long bones including the tibia, fibula, and femur, some of the flat bones at the base of the skull such as the basosphenoid bones, ribs, clavicle, and vertebrae. The intramembranous bones of the maxilla and mandible (alveolar bone) are also positive for asporin. Weak asporin expression is observed in the dermal mesenchyme. A strong signal was observed in sagittal sections of the subcutaneous muscles or panniculus camosus of the thorax, trunk, and head/neck (platysma muscle) region and are shown as arrows in the figure. In this section, very little asporin message was detected in the major parenchymal organs. Furthermore, upon examination of the serial section that was probed with the asporin sense "control" riboprobe, a nonspecific signal was observed in the heart, lung, and liver perhaps due to the nonspecific binding of the probe to the erythrocytes. Nevertheless, a specific signal for asporin was observed in the large bronchi of the lung (arrows pointing to bronchi). The strong expression of asporin in the perichondrium is underscored in a sagittal section of the digits of a 15.5 dpc forelimb (FIG. 5B). Comparisons of dark and bright field micrographs of the distal end of the third digit (FIG. 5C, magnification of 20× at FIG. 5D) show that asporin signal is prominent in the region containing the fibroblasts of the perichondrium. The perichondrium can be separated into two layers, and the mesenchymal cells of the inner layer have the capacity to differentiate into the chondrocyte lineage leading to the appositional growth of cartilage, but the outer layer is composed of fibroblasts that do not have this capacity. Although asporin has a prominent expression in the outer layer, the diffuse signal detected in this procedure does not permit us to conclude that asporin RNA signal is restricted to the outer layer of the perichondrium.

Even though asporin RNA expression is prominent in the developing mouse skeleton, particularly in the perichondrium/periosteum of cartilage/bone, it is also found in other specialized connective tissues such as tendon, sclera, the connective tissue sheath surrounding muscle, and dermis. Tendon and scleral expression of asporin is shown in FIGS. 6A and 6B, respectively.

Sagittal sections of specialized connective tissues at different stages of mouse embryonic development probed with an asporin anti-sense riboprobe. Bright field images are shown to the right of dark field images. FIG. 6A: Asporin expression in tendon (Te) and the perichondrium/periosteum of scapula (Sp) and humerus (Hu) at 15.5 dpc. FIG. 6B: Asporin expression in the eye is restricted to the sclera (Sc) at 17.5 dpc (albino mouse). FIG. 6C: Asporin expression in connective tissues of tongue at 18.5 dpc: (1) the lamina propria (Lp) underlying the tongue epithelia; (2) lingual fascia (Lf) or connective tissue sheath surrounding the muscle bundles of the tongue. The positive asporin signal for the fascia appears as parallel striations in the section and the muscle fibers do not give a positive signal. The lower surface of the tongue faces the mandible (Mn). FIG. 6D: Asporin expression in dissected skin from an 18.5 dpc embryo is detected in the dermis (Dm) but not in the epidermis (Ep).

Figure 6:
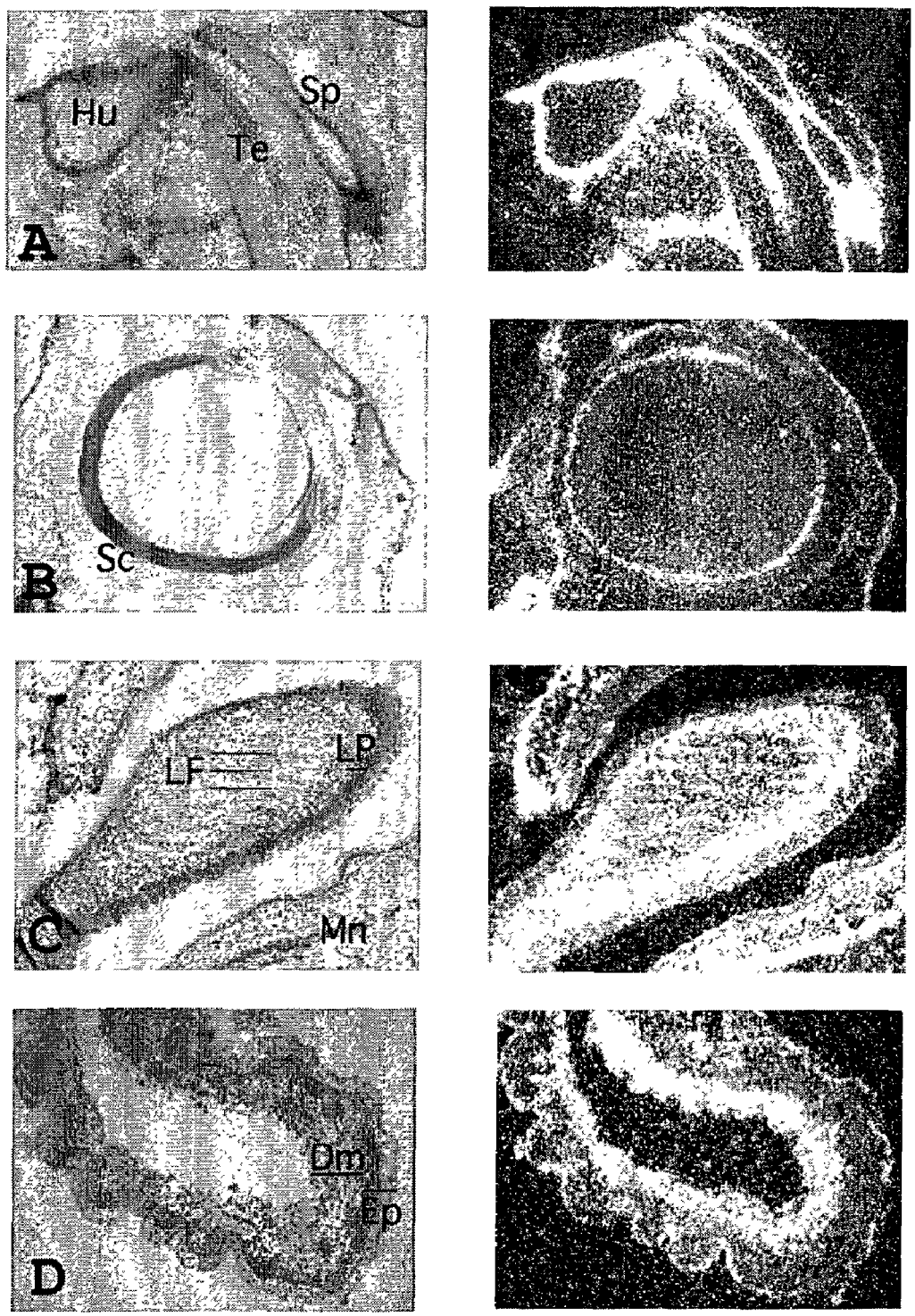
FIG. 6A shows expression of asporin in the tendon.
FIG. 6B shows scleral expression of asporin.
FIG. 6C is a parasagittal section of the tongue at 18.5 dpc.
FIG. 6D are skin shavings. |
| 7 | Diagram showing a 188 kb region of three overlapping BAC clones. |
| 8 | Dendrogram of the SLRP gene family. |
| 9 | Schematic depiction of three SLRP clusters. |

Parasagittal sections of the tongue at ME 18.5 dpc reveals that the connective tissue layer of the lamina propria and the lingual fascia ensheathing the striated skeletal muscle bundles of the tongue are positive for asporin RNA expression (FIG. 6C). The positive signal for the fascia or the connective tissue sheath surrounding the interlacing bundles of striated skeletal muscles appears as parallel striations in the center of the section, and the myofibers are negative. Prior to embedding the 18.5 dpc embryos during the in situ hybridization protocol, the skin is peeled away from the embryo to allow for adequate penetration of fixatives. Surreptitiously, some skin shavings remained on the slide during the procedure, and positive signal for asporin was observed in the dermis but not in the epidermis (FIG. 6D). The signal appears to be strongest in the deep reticular layer of dermis rather than the superficial papillary layer of dermis. Since the expression of asporin was observed from dissected skin, it is difficult to localize asporin RNA expression to a specific layer of dermis. The ribs and the pectoral muscle at ME 18.5 dpc (FIG. 6E) are positive (as mentioned previously, the overlying skin has been removed). Since the myofibers of the tongue are negative for asporin RNA expression at 18.5 dpc, it is likely that the positive signal of asporin detected in the subcutaneous muscles of the sagittally sectioned 15.5 dpc embryo (FIG. 5) arises within the connective tissue sheathes surrounding the muscles rather than the muscle fibers. In summary, during mouse embryonic development, asporin mRNA expression was detected primarily in the skeleton and other specialized connective tissues, but very little asporin message was detected in the major parenchymal organs.

Gene Structure of Asporin

A mouse bacterial artificial library (BAC) was screened with an asporin probe and two unique BAC clones were obtained. Purified BAC DNA was used as template to PCR-amplify the introns of the mouse asporin gene in a long distance PCR strategy. The amplified introns were resolved electrophoretically on an ethidium bromide-stained 0.8% agarose gel, and their sizes were estimated. The seven introns were subcloned and the exon/intron junctions were sequenced. The mouse asporin gene spans about 23 kilobases and contains 8 exons.

The gene structure of human asporin was determined by alignment of annotated nucleotide sequence from genomic BAC clone AL137848 with overlapping human ESTs. The human gene spans about 25 kb and also contains 8 exons. The size of the first exon was determined by nucleotide sequencing the largest PCR-amplified product from 5' RACE reactions. The size of the last exon was determined by comparing all the overlapping asporin 3' ESTs available on the public databases and choosing the ones that were the longest in the 3' direction.

The gene size and structure of asporin in both species examined are very similar. The largest intron for both genes is the first, whereas the smallest intron is the sixth. The codon phasing at the exon/intron boundaries of the mouse and human genes is identical, and the intron sizes are similar.

Asporin is part of a SLRP gene cluster on human chromosome 9. The nucleotide sequence of three overlapping human BAC clones (AL157827, AL137848, and AL354924) localized to chromosome 9q22-9q21.3 was subsequently annotated.

Figure 7:

A diagram depicting a 188 kb region of three overlapping BAC clones is shown in FIG. 7. Annotation of the nucleic acid sequences of three BAC clones afforded the genomic organization of ECM2, asporin, osteoadherin, and osteoglycin on human chromosome 9q21.3-9q22. Wherever possible, comparison was made between overlapping clones. However, it was necessary to determine the location and direction of 16 kb of one contig in the center of AL137848, between asporin and osteoglycin, by performing bridging PCR reactions to neighboring contigs. Three gaps within intronic sequences could not be annotated.

This analysis revealed a cluster of 4 genes that code for LRR-containing proteins: ECM2, asporin, osteoadherin, and osteoglycin. In the center of BAC AL137848, between asporin and osteoglycin, it was necessary to determine the location and orientation of a 16 kb contig by performing bridging PCR reactions to neighboring contigs. Three gaps within intronic sequences could not be annotated and are shown as vertical dotted lines in the figure. Within the 188 kb region, the 4 genes are arranged in a head-to-tail fashion with the same transcriptional orientation. The three SLRP genes are physically linked and include one member from each SLRP class: asporin (class I)-osteoadherin (class II)-osteoglycin/mimecan (class III). The 5' and 3' untranslated region of each gene was estimated by comparison with nucleotide sequences contained in human ESTs that exhibited homology specifically to the extreme 5' and 3' ends of the genes.

Figure 8:
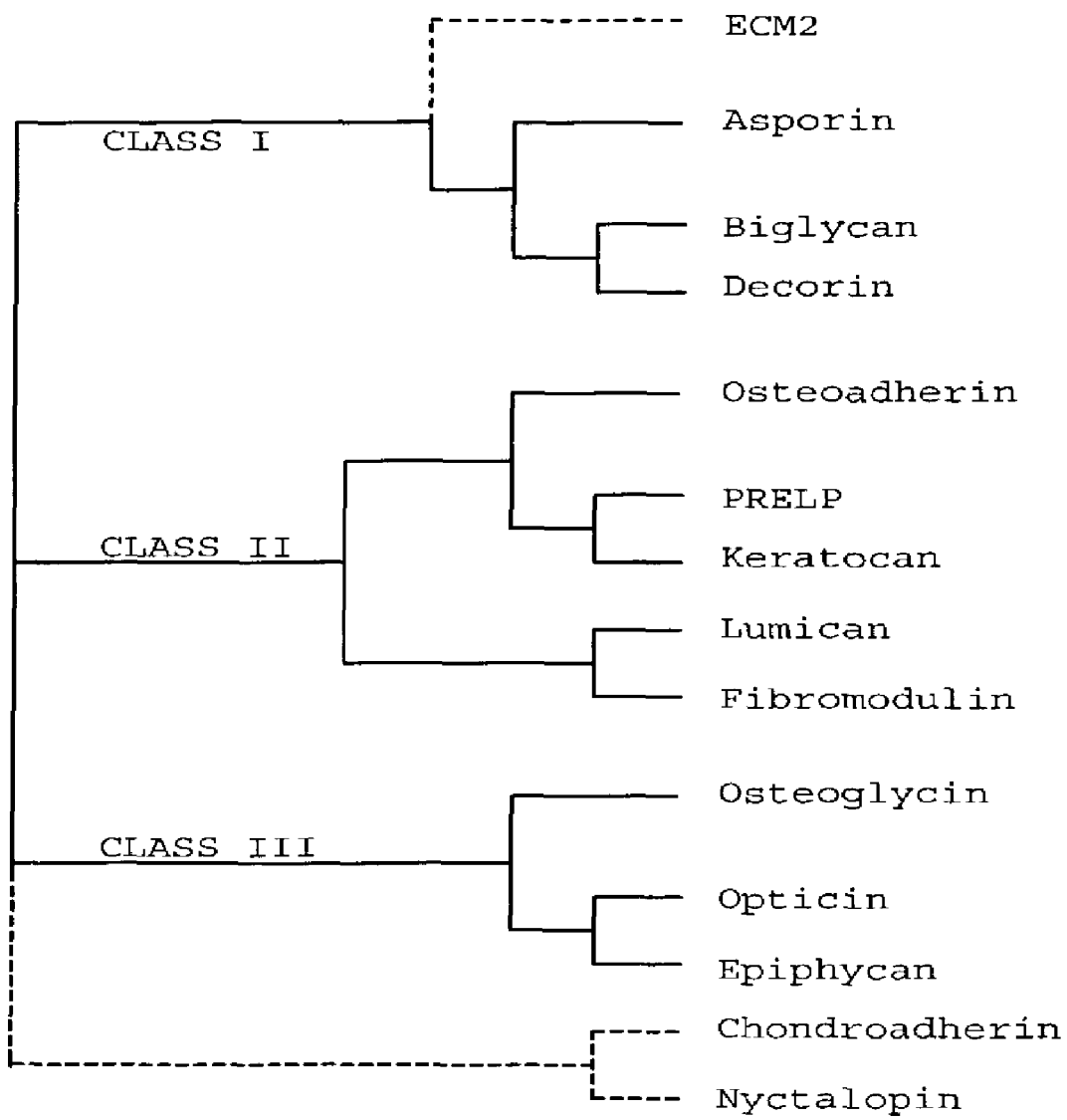

A dendrogram of the SLRP gene family is shown in FIG. 8. This figure is a dendrogram showing predicted relationships between SLRP family members and other LRR proteins of the ECM. Horizontal distances of bars are proportional to evolutionary distance and are based on human protein sequences. The SLRP family is subdivided into 3 classes: class I contains 3 members; class II contains 5 members; and class III contains 3 members. Asporin is a class I member, and biglycan and decorin are more related. Although chondroadherin and the recently identified nyctalopin have been granted membership to the SLRP gene family, they may have diverged from the other three SLRP classes early in evolution because their structures are significantly different from the conventional SLRPs. Likewise, ECM2 is structurally different from the conventional SLRPs, but has a LRR domain that shows some homology with the SLRPs. Since ECM2 is physically linked to asporin on human chromosome 9, it has been included in the dendrogram. This analysis was done with public software using ClustalW version 1.81 (www.ebi.ac.uk/clustalw/) and the output was generated with TreeViewer (taxonomy.zoology.gla.ac.uk/rod/treeview.html).

With the introduction of asporin, 11 members reside in the three SLRP gene family classes. Class I members include asporin, biglycan and decorin; class II includes osteoadherin, lumican, fibromodulin, PRELP and keratocan; class III includes osteoglycin/mimecan, opticin, and epiphycan/PG-Lb. Although chondroadherin and the recently identified nyctalopin (Bech-Hansen, N. T., et al. (2000) Nat. Genet.

26(3), 319-323; Pusch, C. M., et al. (2000) Nat. Genet. 26(3), 324-327) have been granted membership to the SLRP gene family, they may have diverged from the other three SLRP classes early in evolution. The gene structure, type of LRRs, and the number and spacing of cysteine residues in the C-terminal region of chondroadherin is different from the other 3 SLRP classes (Neame, P. J., et al. (1994) J. Biol. Chem. 269(34), 21547-21554; Grover, J., et al. (1997) Genomics 45(2), 379-385). Human ECM2 (Nishiu, J., et al. (1998) Genomics 52(3), 378-381) is substantially larger than the SLRPs (a translated human ORF of 699 amino acids), but contains a LRR domain that shares 34% amino acid identity with the corresponding region in human decorin. In any event, ECM2 is physically linked to asporin on human chromosome 9 and has been included in the dendrogram.

The size and amino acid sequence of the asporin protein are remarkably similar to those of the core proteins of the other members of the class I subfamily, decorin and biglycan. Almost 70% of the residues in these proteins are identical or conserved. Furthermore, they all contain 10 highly conserved LRRs in the central region, and the number and amino acid spacing of the cysteine residues in the N- and C-terminal domains are conserved. The region of the class I proteins that is least similar lies N-terminal to the first cysteine cluster. For the proteoglycans decorin and biglycan, the serine/glycine dipeptide sequence(s) required for xylosyl transfer and glycosoaminoglycan attachment are located in this region. Asporin does not contain this dipeptide, thus asporin is probably not a proteoglycan. Instead, asporin contains a stretch of aspartate residues in this region. This acidic motif in the human is composed of 18 residues and in the mouse the motif is 7 residues shorter. Two other identified SLRPs, osteoadherin and epiphycan have acidic regions. In epiphycan, this stretch is composed of aspartic acid residues and interestingly the acidic motif in human and bovine sequences (Deere, M., et al. (1996) Genomics 38(3), 399-404; Johnson, H. J., et al. (1997) J. Biol. Chem. 272, 18709-18717) is longer than the corresponding motif in the mouse sequence (Kurita, K., et al. (1996) Biochem. J. 318(Pt 3), 909-914). The C-terminal region of osteoadherin is rich in both aspartic and glutamic acid residues (Wendel, M., et al. (1998) J. Cell. Biol. 141(3), 839-847). The importance of these acidic motifs is unclear. Since these motifs are present in molecules that primarily are not proteoglycans (with the possible exception of epiphycan), it is tempting to speculate that the acidic motifs act as "pseudoglycosaminoglycans" and substitute for the acidic polysaccharides in the proteoglycans.

All the members of the class I SLRP subfamily appear to have a relatively broad tissue distribution in the adult mouse, but this distribution is not completely overlapping. For example, Northern blot analysis indicates that biglycan has appreciable mRNA expression in the lung, whereas decorin signal is particularly strong in the skin. Asporin appears to have the most restricted tissue distribution and many tissues such as liver, brain, and spleen do not give a positive signal. The shorter wash periods and longer film exposure time following the asporin Northern hybridization as compared to the analogous wash and film exposure times following the decorin and biglycan Northern hybridizations, suggest that the mRNA concentration of asporin may be lower than that of decorin and biglycan in the adult organs tested.

Since the primary amino acid sequence of asporin is most similar to decorin and biglycan, it is worthwhile comparing the spatial and temporal expression patterns of asporin to that of decorin and biglycan in mouse embryonic development. During mouse embryonic development, asporin has both unique and overlapping expression patterns compared to its fellow class I members. Interestingly, the RNA expression pattern of biglycan and decorin during human fetal development revealed that the biglycan and decorin expression patterns were "substantially divergent and sometimes mutually exclusive" (Bianco, P., et al. (1990) J. Histochem. Cytochem. 38(11), 1549-1563). Nevertheless, a study of the RNA expression pattern for five SLRP genes during mouse development was recently conducted (Wilda, M., et al. (2000) J. Bone Miner. Res. 15(11), 2187-2196) and partially overlapping RNA expression patterns were observed amongst the five genes studied. At ME 14.5, biglycan is expressed in the mesenchymal surroundings of the vertebrae, ribs, and large bones of the hind limbs, but decorin is not expressed in cartilage and bone (Wilda, M., et al. (2000) J. Bone Miner. Res. 15(11), 2187-2196). At this stage of mouse embryonic development, the RNA expression of asporin in the skeleton, specifically localized to the perichondrium, is similar to biglycan. The RNA expression pattern of biglycan and asporin in the developing cartilage is restricted to the perichondrium at this stage of mouse embryogenesis and is in sharp contrast to the cartilage expression pattern observed for two other SLRPs, epiphycan (Johnson, J. et al. (1999) Dev. Dyn. 216(4-5), 499-510) and chondroadherin (Wilda, M., et al. (2000) J. Bone Miner. Res. 15(11), 2187-2196), which are predominately expressed in the chondrocytes of the central cartilage "proper." Asporin was observed in the periosteum of the long bones at ME 18.5 dpc and biglycan is clearly expressed in the periosteum at 2 days of postnatal development (Wilda, M., et al. (2000) J. Bone Miner. Res. 15(11), 2187-2196). Additional Northern blots will be performed including cartilage and bone to determine the extent, if any, of asporin production in adult mouse cartilage or bone. The strong RNA expression of asporin observed in the fascia surrounding the muscle bundles of the tongue, and presumably the fascia surrounding subcutaneous muscles as well, coincides with a similar connective tissue expression pattern observed for mouse and human decorin. During human fetal development, decorin core protein was localized to the connective tissue sheathes surrounding skeletal myofibers, whereas biglycan core protein was localized to the actual myofibers (Bianco, P., et al. (1990) J. Histochem. Cytochem. 38(11), 1549-1563). Likewise, in the mouse, decorin protein was localized to the perimysium of the subcutaneous muscle (Danielson, K. G., et al. (1997) J. Cell Biol. 136, 729-743). Taken together, during mouse embryogenesis, asporin RNA expression has some overlap with biglycan in the skeleton and some overlap with decorin in the fascia of muscle. Moreover, overlapping RNA expression patterns in the dermal mesenchyme was observed for many SLRPs including decorin, lumican, asporin, and biglycan during mouse embryogenesis, supporting the observation that SLRPs have partially overlapping RNA expression patterns.

The close structural similarity and overlapping tissue distribution suggest that the SLRPs could represent a family of molecules with redundant functions. This hypothesis is supported by the observation that despite the potent in vitro effects of individual SLRPs, analyses of mice with inactivated or deleted genes reveal suprisingly mild phenotypes. In fact, a certain degree of compensation has been seen in these mice. Recently, morphological analysis of early tendon development in mice for the double "knockout" of lumican and fibromodulin reveals an additive phenotypic effect for the double mutant as compared to the single mutants (Ezura, Y., et al. (2000) J. Cell. Biol. 151(4), 779-788). An increased deposition of lumican protein was observed in whole protein extracts of tails from fibromodulin-null mice suggesting that lumican and fibromodulin may share a binding site (Svensson, L., et al. (1999) J. Biol. Chem. 274(14), 9636-9647). Furthermore, biochemical evidence supports the notion that lumican and fibromodulin may share a common binding site on collagen (Svensson, L., et al. (2000) FEBS Lett. 470(2), 178-182). Also, some single SLRP "knockouts" exhibit phenotypes in the same tissues. The decorin-, fibromodulin-, and lumican-null mice (Danielson, K. G., et al. (1997) J. Cell. Biol. 136, 729-743; Svensson, L., et al. (1999) J. Biol. Chem. 274(14), 9636-9647; Ezura, Y., et al. (2000) J. Cell. Biol. 151(4), 779-788) have atendon phenotype, and a skin phenotype is observed in the decorin-null (Danielson, K. G., et al. (1997) J. Cell Biol. 136, 729-743) and lumican-null mice (Chakravarti, S., et al. (1998) J. Cell. Biol. 141(5), 1277-1286). Consequently, the SLRP proteins may have interchangeable functions in certain tissues, and the role of compensation may become more apparent as more SLRP double knockouts are generated and subsequently studied.

Figure 9:
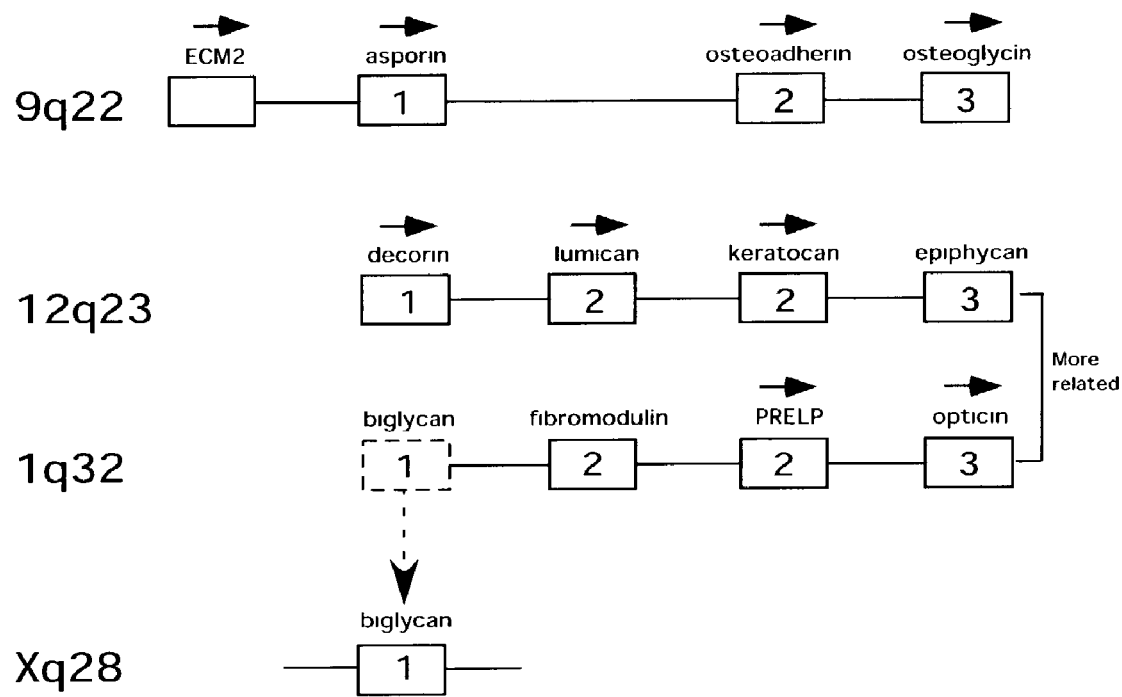

A novel SLRP cluster in mammals and a schematic depiction of three SLRP clusters is shown in FIG. 9. This figure is a diagram depicting the chromosomal organization of the SLRP genes. Three clusters of SLRP genes are represented as horizontal lines with their respective human chromosomal localization shown to the extreme left of the cluster. The genes are depicted as boxes, and the class designation for each SLRP gene (refer to dendrogram, FIG. 8) is shown as a number inside the box. Paralogous genes amongst the clusters are aligned vertically, and the horizontal distance between genes within a cluster are not to scale. If the transcriptional orientation of the genes in the cluster is known, it is shown as an arrow above the box. Upon alignment of the paralogous genes, one can speculate that biglycan may have been part of the cluster that resides on chromosome 1 at an early point in evolution and later migrated to the X-chromosome. If one compares the genetic distance of SLRP class members predicted by the dendrogram (see FIG. 8) with the paralogous genes arranged in the three clusters, it appears that the clusters on chromosome 1 and 12 are more related and may have arisen from a duplication event of a "primordial" cluster.

In this figure, the horizontal distance between genes in a cluster is not to scale. SLRP class 1 gene members lie 5' to class 2 members in a cluster. Likewise, class 3 members lie 3' to class 2 members in a cluster. The transcriptional orientation of the genes is shown by an arrow above the box that represents each gene. The transcriptional orientation of the genes located on chromosome 12 follows published reports (Pellegata, N. S., et al. (2000) Nat. Genet. 25(1), 91-95). The position of human fibromodulin, PRELP and opticin on human chromosome 1q32 was determined by annotation of the nucleotide sequences contained in BACs, AL359837, AC022000, and AL391817.

The class members can be aligned vertically amongst paralogous genes in the three clusters. If the three clusters are aligned based upon the evolutionary distances depicted in the dendrogram tree, it appears that the paralogous genes on chromosomes 1 and 12 are more similar than the paralogous genes on chromosome 1 and 9 or the paralogous genes on chromosome 9 and 12. Therefore, the SLRP genes clustered on human chromosome 9 may have arisen independently from the clusters on chromosome 1 and 12. Perhaps, the clusters on chromosome 1 and 12 arose from a second duplication of a common cluster.

Upon examination of BAC contigs from human chromosome 1q32, we have failed to discover a SLRP class I member close to the fibromodulin gene. Additionally, the biglycan gene on the X-chromosome does not appear to be physically linked to other genes that encode for leucine-rich repeating proteins. With the identification of asporin as a class I member on human chromosome 9, we propose that biglycan may have been previously linked with the SLRP cluster on chromosome 1, but early in evolution the gene migrated from this cluster and came to reside on the X-chromosome.

Most of the SLRP genes are arranged in gene clusters that presumably arose from gene duplication events of a "primordial" cluster early in evolution. Since these genes have been "retained" in the clusters during evolution, it is likely that a degree of functional redundancy has also been "retained." The class I SLRPs have a broad tissue distribution; yet some of the SLRPS have a more restricted expression pattern such as opticin (eye), epiphycan (fetal growth plate cartilage), and osteoadherin (calcified cartilage and bone) and are still retained in the clusters. Perhaps these SLRPs, with more specialized function and restricted tissue distribution, evolved more rapidly than the other genes found in the respective cluster.

The RNA and protein expression pattern of decorin and biglycan appears to be divergent and in some cases completely non-overlapping. However, the identification of a novel class I subfamily member may change our hypothesis concerning functional redundancy amongst class I members. Results suggests that asporin has a partial overlapping RNA expression pattern with decorin and biglycan in mouse embryonic development, and consequently asporin must be considered as a candidate for functional redundancy with decorin and biglycan. Perhaps, asporin gene expression or even asporin protein deposition in the extracellular matrix may be affected in the decorin and/or biglycan-null mice, and this may result in a partial rescue of the phenotype. Ultimately, this needs to be tested, and the production of asporin-null mice needs to be explored. In view of the overlapping expression patterns observed amongst many SLRPs, one can speculate that asporin plays a role in the structural organization or signaling of the extracellular matrix in the skeleton and other specialized connective tissues.

Accordingly, one embodiment of the invention is directed towards an isolated asporin protein. The protein is preferably at least about 90% identical to SEQ ID NO:6 or SEQ ID NO:22 (SEQ ID NO:6 after cleavage of signal sequence SEQ ID NO:21). The protein can be about 90%, about 92%, about 94%, about 96%, about 98%, about 99%, or 100% identical to SEQ ID NO:6 or SEQ ID NO:22. The protein can be an amino acid sequence immunoreactive with an antibody prepared using either SEQ ID NO:6 or SEQ ID NO:22 as an antigen, the antibody being immunoreactive with SEQ ID NO:6 or SEQ ID NO:22. The asporin protein can consist essentially of SEQ ID NO:6 or SEQ ID NO:22, or can consist of SEQ ID NO:6 or SEQ ID NO:22.

An additional embodiment of the invention is directed towards a nucleic acid molecule segment comprising a structural nucleic acid sequence encoding an asporin protein. The structural nucleic acid sequence is preferably at least about 90% identical to SEQ ID NO:2. The structural nucleic acid sequence can be about 90%, about 92%, about 94%, about 96%, about 98%, about 99%, or 100% identical to SEQ ID NO:2. The structural nucleic acid sequence can hybridize under stringent hybridization conditions to the reverse complement of SEQ ID NO:2. Alternatively, the structural nucleic acid sequence can be any that encodes SEQ ID NO:6 or SEQ ID NO:22. The nucleic acid molecule segment can be single stranded or double stranded. The segment can be linear or circular.

A further embodiment of the invention is directed towards a recombinant vector. The vector can comprise operatively linked in the 5' to 3' orientation: a promoter that directs transcription of a structural nucleic acid sequence; a structural nucleic acid sequence, and a 3' transcription terminator. The structural nucleic acid sequence can be any of the structural nucleic acid sequences described above. The promoter can generally be any promoter, such as CaMV 35S, FMV, inducible promoters, and constitutive promoters. The transcription terminator can generally be any transcription terminator, such as NOS.

The invention additionally encompasses recombinant host cells comprising any of the above described structural nucleic acid sequences. The recombinant host cell can generally be any type of host cell, such as bacteria, yeast, insect, plant, or mammalian cells. The copy number of the structural nucleic acid sequence in the recombinant host cell is preferably higher than the copy number of the structural nucleic acid sequence in a wild type host cell of the same species.

The asporin protein allows preparation of antibodies. The antibodies are preferably prepared using SEQ ID NO:6 or SEQ ID NO:22 as an antigen, and are immunoreactive with SEQ ID NO:6 or SEQ ID NO:22. The antibodies can be polyclonal or monoclonal. The antibodies can be prepared by methods well known to those of skill in the art. The antibodies can be used in diagnostic assays such as Western blots and ELISA assays.

Recombinant host cells can be prepared by various methods. For example, the method can comprise selecting a host cell; transforming the host cell with a recombinant vector; and obtaining recombinant host cells. The recombinant vector can generally be any of the above described recombinant vectors. The transforming step can be performed by any method. Multiple methods of transformation are well known to those of skill in the art, such as electroporation, biolistics, chemical or lipid mediated transformation, and viral transformation. The host cell can generally be any type of host cell, such as bacteria, yeast, insect, plant, or mammalian cells. For plant cells, the method may further comprise regeneration of the recombinant plant cells to produce recombinant plants or recombinant plant seeds.

The invention further involves various in vitro and in vivo methods for treating cells, tissues, or organisms with an asporin protein. In all cases, the methods comprise administering an effective amount of asporin to the cells, tissue, or organism to achieve the desired effect. The dosage may vary depending on the desired result, and the material treated, but are readily determined by one of skill in the art without excessive experimentation. The dosages may be in a single dose format, a multiple dose format, or a constant delivery format. The methods include regulating the complement system, inhibiting fibrosis formation, regulating the growth of endothelial cells and angiogenesis, regulating or inhibiting the growth of cancer cells, and regulating the functions of neuromuscular junctions. Regulation can be positive regulation or negative regulation.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

Example 1

Materials

Chemicals and supplies were purchased from Sigma, Fisher, and Intermountain Scientific. Total RNA was extracted from confluent mouse ATDC5 cells (Atsumi, T., et al. (1990) Cell. Differ. Dev. 30(2), 109-16) by using the QIAshredder kit and was purified with the RNAeasy mini kit (QIAGEN, Germany). Total human heart RNA was obtained from Ambion (Austin, Tex., USA). Reverse transcription reactions were performed with Superscript II reverse transcriptase (Gibco BRL, Rockville, Md., USA), and first strand cDNA was synthesized by 5' and 3' rapid amplification of cDNA ends (5' and 3' RACE) using SMART™ (Switch Mechanism At the 5' end of RNA Templates) technology (Clontech). The QIAPREP spin miniprep kit and the QIAEX II gel extraction kit (QIAGEN, Germany) were used to purify DNA.

The plasmid vector used in subcloning was pBluescriptKS (Stratagene, La Jolla, Calif., USA). Nucleotide sequencing reactions were performed on a Perkin Elmer DNA analysis apparatus (model #377) with the PRISM™ Ready Reaction Dye Terminator Cycle Sequencing kit (Perkin Elmer Applied Biosystems, Foster City, Calif., USA). Oligonucleotides were synthesized and purchased from Sigma-Genosys. Polymerase chain reactions (PCR) were performed with one of the following polymerases: Taq polymerase (Gibco BRL), Advantage 2 Polymerase Mix (Clontech, Palo Alto, Calif., USA), Pfu Polymerase (Stratagene) or Takara LA Taq™ polymerase (Takara Biomedicals, Japan). PCR products were ligated into a TA-cloning vector (Marchuk, D., et al. (1991) Nucleic Acids Res. 19, 1154) or the pGEM® T-easy vector system (Promega).

The mouse poly A+ multiple tissue Northern blot was from OriGene Technologies, Inc. The nylon membranes used to screen the mouse bacterial artificial chromosomal (BAC) library were from Research Genetics (Alabama, USA). Radioisotopes-[$\alpha$-$^{32}$P]dATP and [$\alpha$-$^{32}$P]dCTP were purchased from Dupont New England Nuclear. Random labeling kits-T7 QuickPrime kit (Amersham Pharmacia) and DNA Strip-EZ (Ambion, Austin Tex.) kit were used. Hybridization fluids used are either Rapid-Hyb (Amersham Pharmacia) or UltraHyb (Ambion). Imaging film and emulsion were purchased from Kodak (X-OMAT-AR film and NTB-2 emulsion.)

Example 2

Cloning Full-length Mouse cDNA

The full-length mouse cDNA was obtained by aligning nucleotide sequences of overlapping PCR products from 5' and 3' rapid amplification of cDNA ends (RACE) reactions. Total RNA was extracted from confluent mouse ATDC5 cells with the QIAshredder kit and was purified with the RNAeasy miniprep kit (QIAGEN). First-strand cDNA was synthesized by reverse transcriptase SuperScript II (Gibco BRL) using the reagents provided in the SMART™ RACE cDNA amplification kit (Clontech). The gene specific primers for mouse asporin were designed from nucleotide sequence contained in expressed sequence tags (ESTs) that were publicly available on GenBank databases.

For 5' RACE reactions, reverse oligonucleotide primers were designed against mouse EST GenBank accession #AI 006670 (MS ASP RV 406: 5'-AGGCTTCACTG-GCTCTTTCGTAGGAAAAAG-3' (SEQ ID NO:27) and MS ASP RV 343: 5'-CGTCATCATCTGTGTCTTC-CATATCCTTC-3' (SEQ ID NO:28)). For 3' RACE reactions, forward oligonucleotides were designed against mouse EST GenBank accession #AA980962 (MS ASP FW 983: 5'-CTTGAAGATCTTAAACGGTACAGG-GAACTGC-3' (SEQ ID NO:29) and MS ASP FW 1077: 5'-CCACGTGTGAGAGAGATACACTTGGAACAC-3' (SEQ ID NO:30)).

First round PCR conditions for 5' and 3' RACE were as follows: the template-RACE ready cDNA; gene specific oligonucleotides-MS ASP RV 406 (5' RACE) and MS ASP FW 983 (3' RACE.); 25 cycles (5 seconds at 94° C., 10 seconds at 60° C., 2 minutes at 72° C.). First round PCR products were diluted and used as template in a second round "nested" PCR as recommended by the kit. Nested PCR products for 14 clones harboring 5' RACE products were resolved electrophoretically on an ethidium bromide-stained 1% agarose gel.

Five of the plasmids containing 5' RACE products of different sizes were sequenced in both directions using the T3 and T7 primers. The largest fragment was called p329, and was used in subsequent Northern, Southern, and in situ hybridization experiments. Also, two clones harboring 3' RACE products of identical size were sequenced in both directions using the T3 and T7 primers.

Since the complete open reading frame (ORF) for mouse asporin could not be determined by alignment of overlapping mouse ESTs, two primers (Ms Start FW: 5'-CGCG-GATCCAAACCCTTCTTTAGCCCTTCCCAC-3' (SEQ ID NO:31); Ms Stop RV: 5'-CGCGGGATCCTTATTTTCCAA-CATTCCCAAGCTG-3' (SEQ ID NO:32)) were designed to amplify by PCR the mouse asporin ORF [template of mouse RACE-ready cDNA, Pfu polymerase, 20 cycles (20 seconds at 94° C., 30 seconds at 60° C., 2 minutes at 72° C.] The amplified mouse asporin ORF was digested with BamHI restriction enzyme and was ligated to BamHI-cleaved pBluescript KS+. The resulting subcloned ORF plasmid was sequenced with three primers: T3, T7, and MS FW 775 (5'-GGACACGTTCAAGGGAATGAATGC-3' (SEQ ID NO:33)) to determine the open reading frame of mouse asporin.

Example 3

Human Partial cDNA

Human heart RNA (Ambion) was reverse transcribed to first strand cDNA by using the SMART™ RACE cDNA amplification kit (Clontech). A partial human cDNA was obtained that contained the open reading frame, the 5' untranslated region, and the transcription start site. The gene specific primers for human asporin were designed from nucleotide sequence contained in human ESTs, AK000136, FLJ20129, and AI539334. PCR conditions are as follows: template-human RACE ready cDNA; gene specific oligonucleotides HU ASP RV STOP (5'-CCGCTCGAGTTACAT-TCCAAAGTTCCCAAGCTGAAC-3' (SEQ ID NO:34) and HU ASP RV 1503 (5'-ACTGCAATAGATGCT-TGTTTCTCTCAACCC-3' (SEQ ID NO:35)); 30 cycles (5 seconds at 94° C., 10 seconds at 60° C., 2 minutes at 72° C.) PCR-amplified products from first round 5' RACE reactions were sequenced.

Example 4

Northern Hybridization

Three separate Northern hybridizations were performed on a single mouse multi-tissue poly A+ RNA blot (Origene). DNA fragments of mouse asporin, biglycan, and decorin cDNAs were random-labeled in separate Northern hybridizations. The asporin probe (p329) is a 478 base pair (bp) PCR-amplified 5' RACE product that encodes for the 5' end of the mouse asporin cDNA that includes the 5' untranslated region (region of cDNA that is encoded by exon I) and a portion of the open reading frame (a fragment of the cDNA that is encoded by exon 2.) The biglycan probe (p368) is a 731 bp PCR-amplified fragment that encodes for a portion of the 3' untranslated region of mouse biglycan (Wegrowski, Y., et al. (1995) Genomics 30(1), 8-17). PCR parameters were as follows: primers are MS BGN3 5'-CCTGAGACCCT-GAACGAACTTCACCTGG-3' (SEQ ID NO:36) and MS BGN4 5'-CGGTGGCAGTGTGCTCTATCCATCTTTCC-3' (SEQ ID NO:37); template is mouse RACE-ready cDNA as described previously, 30 cycles (20 seconds at 94° C., 20 seconds at 60° C., 1 minute at 72° C.)]. The decorin probe (p280) is a 399 bp XbaI/HindIII fragment from the 3' end of the mouse decorin open reading frame (Scholzen, T., et al. (1994) J. Biol. Chem. 269(45), 28270-28281).

DNA probes were random-labeled by using the Strip-EZ™ kit (Ambion). Following an overnight hybridization at 42° C., the blot was washed under high stringency (1% SDS, 2×SSC) at 65° C. The same blot was subjected to 3 separate Northern hybridizations in this sequence-asporin hybridization, strip blot of probe, decorin hybridization, strip blot of probe, and biglycan hybridization. Radiolabeled probes were removed using Ambion's Strip-EZ technology between consecutive hybridizations. The wash conditions following each hybridization are as follows: asporin-2 washes of 5 minutes, film exposure 16 hours; decorin-2 washes of 30 minutes, film exposure 2 hours; biglycan-3 washes of 10 minutes, film exposure 7 hours. Radioactive Northern blots were exposed to Kodak film (X-OMAT AR).

Example 5

Mouse Gene Structure

A PCR-amplified 5' RACE product (p329) described earlier was used as a radiolabeled probe in a Southern hybridization to screen a mouse genomic BAC library (Research Genetics). After an overnight hybridization at 65° C., the blots were washed under high stringency (1% SDS, 2×SSC) at 65° C. (3×15 minutes) and exposed to X-ray film. Two BAC clones corresponding to positive signals seen on the developed film were acquired from Research Genetics.

After annotation of the genomic nucleotide sequence from BAC #AL137848, the exon/intron boundaries of the human asporin gene were determined by aligning homologous regions of this sequence with sequence from available human ESTs. Assuming that the mouse gene structure is likely to be similar to the human gene structure, the regions in the mouse cDNA that encoded for exons in the mouse gene were predicted. Forward and reverse primers were designed from regions in the mouse cDNA that were predicted to encode for consecutive exons (i.e., forward primer in exon 1, reverse primer in exon 2). With purified mouse BAC DNA as template, such primer pairs were used in long distance PCR reactions to amplify the introns of the mouse asporin gene. Amplified fragments were separated by electrophoresis on an ethidium bromide-stained 0.8% agarose gel to judge intron size and were subcloned using the pGEM® T-easy vector system. Subcloned fragments were sequenced with the T7 and SP6 primers to determine the sequence of the mouse exon/intron boundaries. The primer pairs used to amplify the introns of the mouse asporin gene are as follows:

For Intron 1:
Asp Ex1 Fw38-5'-GCACATAGAGGCTGTTAG-GAGGGCTGG-3' (SEQ ID NO:38)
Asp Ex2 Rv343-5'-CGTCATCATCTGTGTCTTCCATATC-CTTC-3' (SEQ ID NO:39)
For Intron 2:
Asp Ex2 Start 5'-CGCGGATCCAAACCCTTCTTTAGC-CCTTCCCAC-3' (SEQ ID NO:40)
Asp Ex3 Rv 5'-CGAGTATCAAATGGAATGTTGTTTG-GAACCG-3' (SEQ ID NO:41)
For Intron 3:
Asp Ex3 Fw 5'-GCGTTCCAAACAACATTC-CATTTGATACTCG-3' (SEQ ID NO:42)
Asp Ex4 Rv 5'-GTTGGTTGTGGGATAAATATAGCCT-TCTC-3' (SEQ ID NO:43)
For Intron 4:
Asp Ex4 Fw 5'-GAGAAGGCTATATTTATCCCACAAC-CAAC-3' (SEQ ID NO:44)
Asp Ex5 Rv 5'-CCCTGGTTCTATCCCGTTGTTCTCAA-GAGG-3' (SEQ ID NO:45)
For Intron 5:
Asp Ex5 Fw 5'-CCTCTTGAGAACAACGGGATAGAAC-CAGGG-3' (SEQ ID NO:46)
Asp Ex6 Rv-5'-CTTTGCAGTTCCCTGTACCGTTTAA-GATC-3' (SEQ ID NO:47)
For Intron 6:
Asp Ex6 Fw 5'-CTTGAAGATCTTAAACGGTACAGG-GAACTGC-3' (SEQ ID NO:48)
Asp Ex7 Rv 5'-GAGTTCCAAGTGTATCTCTCTCA-CACGTGG-3' (SEQ ID NO:49)
For Intron 7:
Asp Ex7 Fw 5'-CCACGTGTGAGAGAGATACACTTG-GAACAC-3' (SEQ ID NO:50)
Asp Ex8 Stop 5'-CGCGGATCCTTATTTTCCAACATTC-CCAAGCTG-3' (SEQ ID NO:51)

Cycling parameters were as follows: template, 25 nanograms of purified BAC DNA, primers at a final concentration of 1 µM, Takara LA Taq™ polymerase, 25 cycles (10 seconds at 98° C., 6 minutes at 66° C.).

Example 6

Human Gene Structure of Asporin

During annotation of the nucleotide sequence from BAC #AL137848, the exon/intron boundaries of the human asporin gene were established by aligning homologous regions of the genomic sequence with available human ESTs (i.e. AK000136, FLJ20129, and AI539334), and determining the regions in the human cDNA that encoded for exons in the human gene. The ENSEMBL web site on the Sanger Centre server confirmed the location of an open reading frame (ENST00000026531) in BAC #AL 137848 that we have named asporin.

Example 7

RNA In Situ Hybridization

In situ hybridizations were performed on sections from different stages of mouse embryos. Sections were hybridized with [$^{35}$S] UTP-labeled antisense or sense RNA probes generated from the plasmid p329 that contains the extreme 5' end of the mouse asporin cDNA (1-478 bp).

Pregnant C57B1 mice were sacrificed on various days post coitus (dpc), embryos were harvested, rinsed in PBS-DEPC, and fixed in 10% (v/v) formalin in PBS for 2-25 hours. The fixed tissues were dehydrated through a series of increasing ethanol concentrations and then cleared in xylene before being embedded in paraffin. Sections of 7 micron in thickness were mounted onto Superfrost Plus slides (Fisher Scientific, Pittsburgh, Pa.). Demineralization was performed by placing the tissue into a solution of 0.1 M Na-phosphate, pH 6.5 containing 0.26 M EDTA for 2-3 days at room temperature with several changes in between. The tissue was rinsed in DEPC-H$_2$O, then dehydrated through a graded series of ethanol concentrations, and embedded and sectioned as described for embryonic tissue.

In situ hybridization was performed essentially as described previously (Zhao, Q., et al. (1997) Dev. Dyn. 209(4), 377-386). Hybridization was carried out at 50° C. for 16-17 hours. Two high stringency washes were performed at 55° C. in 50% formamide, 2×SSC for 20 minutes each. Autoradiography was carried out using NTB-2 Kodak emulsion. The slides were exposed for 16 hours to 7 days at 4° C. Microphotographs were taken using both bright and dark-field optics.

Example 8

Future Generation Asporin Sequences

For future variations of the asporin protein, in addition to the coding sequences for the protein from other organisms, coding sequences showing high similarity to the coding sequence could be used in producing asporin proteins.

Sources other than mouse may be used to obtain the sequences used to produce an asporin nucleic acid sequence, and the encoded asporin protein. For example, sequences from humans, dogs, cats, pigs, horses, cows, moose, bears, rats, or other organisms could be used as a source of protein or nucleic acid sequences. Furthermore, subunit sequences from different organisms may be combined to create a novel asporin sequence incorporating structural, regulatory, and enzymatic properties from different sources.

Example 9

Nucleic Acid Mutation and Hybridization

Variations in the nucleic acid sequence encoding an asporin protein may lead to mutant asporin protein sequences that display equivalent or superior enzymatic characteristics when compared to the sequences disclosed herein. This invention accordingly encompasses nucleic acid sequences which are similar to the sequences disclosed herein, protein sequences which are similar to the sequences disclosed herein, and the nucleic acid sequences that encode them. Mutations may include deletions, insertions, truncations, substitutions, fusions, shuffling of subunit sequences, and the like. Mutations to a nucleic acid sequence may be introduced in either a specific or random manner, both of which are well known to those of skill in the art of molecular biology. A myriad of site-directed mutagenesis techniques exist, typically using oligonucleotides to introduce mutations at specific locations in a nucleic acid sequence. Examples include single strand rescue (Kunkel, T. *Proc. Natl. Acad. Sci. USA.*, 82: 488-492, 1985), unique site elimination (Deng and Nickloff, *Anal. Biochem.* 200: 81, 1992), nick protection (Vandeyar, et al. *Gene* 65: 129-133, 1988), and PCR (Costa, et al. *Methods Mol. Biol.* 57: 31-44, 1996). Random or non-specific mutations may be generated by chemical agents (for a general review, see Singer and Kusmierek, *Ann. Rev. Biochem.* 52: 655-693, 1982) such as nitrosoguanidine (Cerda-Olmedo et al., *J. Mol. Biol.* 33: 705-719, 1968; Guerola, et al. *Nature New Biol.* 230: 122-125, 1971) and 2-aminopurine (Rogan and Bessman, *J. Bacteriol.* 103: 622-633, 1970), or by biological methods such as passage through mutator strains (Greener et al. *Mol. Biotechnol.* 7: 189-195, 1997).

Nucleic acid hybridization is a technique well known to those of skill in the art of DNA manipulation. The hybridization properties of a given pair of nucleic acids is an indication of their similarity or identity. Mutated nucleic acid sequences may be selected for their similarity to the disclosed nucleic acid sequences on the basis of their hybridization to the disclosed sequences. Low stringency conditions may be used to select sequences with multiple mutations. One may wish to employ conditions such as about 0.15 M to about 0.9 M sodium chloride, at temperatures ranging from about 20° C. to about 55° C. High stringency conditions may be used to select for nucleic acid sequences with higher degrees of identity to the disclosed sequences. Conditions employed may include about 0.02 M to about 0.15 M sodium chloride, about 0.5% to about 5% casein, about 0.02% SDS and/or about 0.1% N-laurylsarcosine, about 0.001 M to about 0.03 M sodium citrate, at temperatures between about 50° C. and about 70° C. More preferably, high stringency conditions are 0.02 M sodium chloride, 0.5% casein, 0.02% SDS, 0.001 M sodium citrate, at a temperature of 50° C.

Example 10

Determination of Homologous and Degenerate Nucleic Acid Sequences

Modification and changes may be made in the sequence of the proteins of the present invention and the nucleic acid segments which encode them and still obtain a functional molecule that encodes a protein with desirable properties. The following is a discussion based upon changing the amino acid sequence of a protein to create an equivalent, or possibly an improved, second-generation molecule. The amino acid changes may be achieved by changing the codons of the nucleic acid sequence, according to the codons given below.

Codon degeneracies of amino acids

| Amino acid | One letter | Three letter | Codons |
|---|---|---|---|
| Alanine | A | Ala | GCA GCC GCG GCT |
| Cysteine | C | Cys | TGC TGT |
| Aspartic acid | D | Asp | GAC GAT |
| Glutamic acid | E | Glu | GAA GAG |
| Phenylalanine | F | Phe | TTC TTT |
| Glycine | G | Gly | GGA GGC GGG GGT |

-continued

Codon degeneracies of amino acids

| Amino acid | One letter | Three letter | Codons |
|---|---|---|---|
| Histidine | H | His | CAC CAT |
| Isoleucine | I | Ile | ATA ATC ATT |
| Lysine | K | Lys | AAA AAG |
| Leucine | L | Leu | TTA TTG CTA CTC CTG CTT |
| Methionine | M | Met | ATG |
| Asparagine | N | Asn | AAC AAT |
| Proline | P | Pro | CCA CCC CCG CCT |
| Glutamine | Q | Gln | CAA CAG |
| Arginine | R | Arg | AGA AGG CGA CGC CGG CGT |
| Serine | S | Ser | AGC AGT TCA TCC TCG TCT |
| Threonine | T | Thr | ACA ACC ACG ACT |
| Valine | V | Val | GTA GTC GTG GTT |
| Tryptophan | W | Trp | TGG |
| Tyrosine | Y | Tyr | TAC TAT |

Certain amino acids may be substituted for other amino acids in a protein sequence without appreciable loss of enzymatic activity. It is thus contemplated that various changes may be made in the peptide sequences of the disclosed protein sequences, or their corresponding nucleic acid sequences without appreciable loss of the biological activity.

In making such changes, the hydropathic index of amino acids may be considered. The importance of the hydropathic amino acid index in conferring interactive biological function on a protein is generally understood in the art (Kyte and Doolittle, *J. Mol. Biol.*, 157: 105-132, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics. These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

It is also understood in the art that the substitution of like amino acids may be made effectively on the basis of hydrophilicity. U.S. Pat. No. 4,554,101 (Hopp, T. P., issued Nov. 19, 1985) states that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0±1); serine (+0.3); asparagine/glutamine (+0.2); glycine (0); threonine (−0.4); proline (−0.5±1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4).

It is understood that an amino acid may be substituted by another amino acid having a similar hydrophilicity score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

As outlined above, amino acid substitutions are therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine, and isoleucine. Changes which are not expected to be advantageous may also be used if these resulted in functional asporin fusion proteins.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope and concept of the invention.

What is claimed is:

1. An isolated protein consisting of the amino acid sequence shown in SEQ ID NO: 22.

* * * * *